(12) United States Patent
Bonny et al.

(10) Patent No.: US 10,131,690 B2
(45) Date of Patent: Nov. 20, 2018

(54) C6S SPECIFIC TRANSPORTER MOLECULES

(71) Applicant: PHI PHARMA SA, Sion (CH)

(72) Inventors: Christophe Bonny, Avenches (CH);
Fabrice Chenaux, Montmollin (CH);
Vincent Zoete, Morges (CH)

(73) Assignee: PHI PHARMA SA, Sion (CH)

( * ) Notice: Subject to any disclaimer, the term of this patent is extended or adjusted under 35 U.S.C. 154(b) by 0 days.

(21) Appl. No.: 15/306,572

(22) PCT Filed: Apr. 27, 2015

(86) PCT No.: PCT/EP2015/059028
§ 371 (c)(1),
(2) Date: Oct. 25, 2016

(87) PCT Pub. No.: WO2015/162285
PCT Pub. Date: Oct. 29, 2015

(65) Prior Publication Data
US 2017/0137465 A1    May 18, 2017

(30) Foreign Application Priority Data
Apr. 25, 2014   (EP) .................................. 14165945

(51) Int. Cl.
*A61K 38/03* (2006.01)
*A61K 47/64* (2017.01)
*C07K 7/06* (2006.01)
*C07K 19/00* (2006.01)
*A61K 38/00* (2006.01)

(52) U.S. Cl.
CPC ............... *C07K 7/06* (2013.01); *A61K 38/03* (2013.01); *A61K 47/64* (2017.08);
(Continued)

(58) Field of Classification Search
CPC ........ A61K 38/03; A61K 47/62; A61K 47/64; A61K 47/6455; C07K 7/06; C07K 2319/01; C07K 2319/035; C07K 2319/20
See application file for complete search history.

(56) References Cited

U.S. PATENT DOCUMENTS 9,688,723 B2 * 6/2017 Bonny .................... C07K 7/06

FOREIGN PATENT DOCUMENTS

| WO | 2009021289 A1 | 2/2009 |
| WO | 2013034982 A2 | 3/2013 |
| WO | 2014041505 A1 | 3/2014 |

OTHER PUBLICATIONS

Moehle et al. Design of beta-Hairpin Peptidomimetics That Inhibit Binding of alpha-Helical HIV-1 Rev Protein . . . Angewandt Chemie, Int. Ed. 2007, vol. 46, pp. 9101-9104.*
(Continued)

*Primary Examiner* — Jeffrey E. Russel
(74) *Attorney, Agent, or Firm* — Jonathan D. Ball; Greenberg Traurig, LLP

(57) ABSTRACT

The present invention relates to isolated molecules, peptides, and polypeptides of specific consensus sequences or structures, and to compounds comprising or consisting of such molecules, peptides or polypeptides, that function as transporter moieties or compositions specifically recognizing the proteoglycan, chondroitin 6-sulfate (C6S). The isolated molecules, peptides, polypeptides and compounds of the invention may be conjugated or otherwise linked to a biologically active moiety (BAM). Thus the BAM conjugates allow the specific targeting and delivery of the BAM, which may be, for example, a peptide, chemical entity or nucleic acid, into the cytoplasm and/or nuclei of C6S expressing cells in vitro and in vivo.

20 Claims, 9 Drawing Sheets

Figure 1:
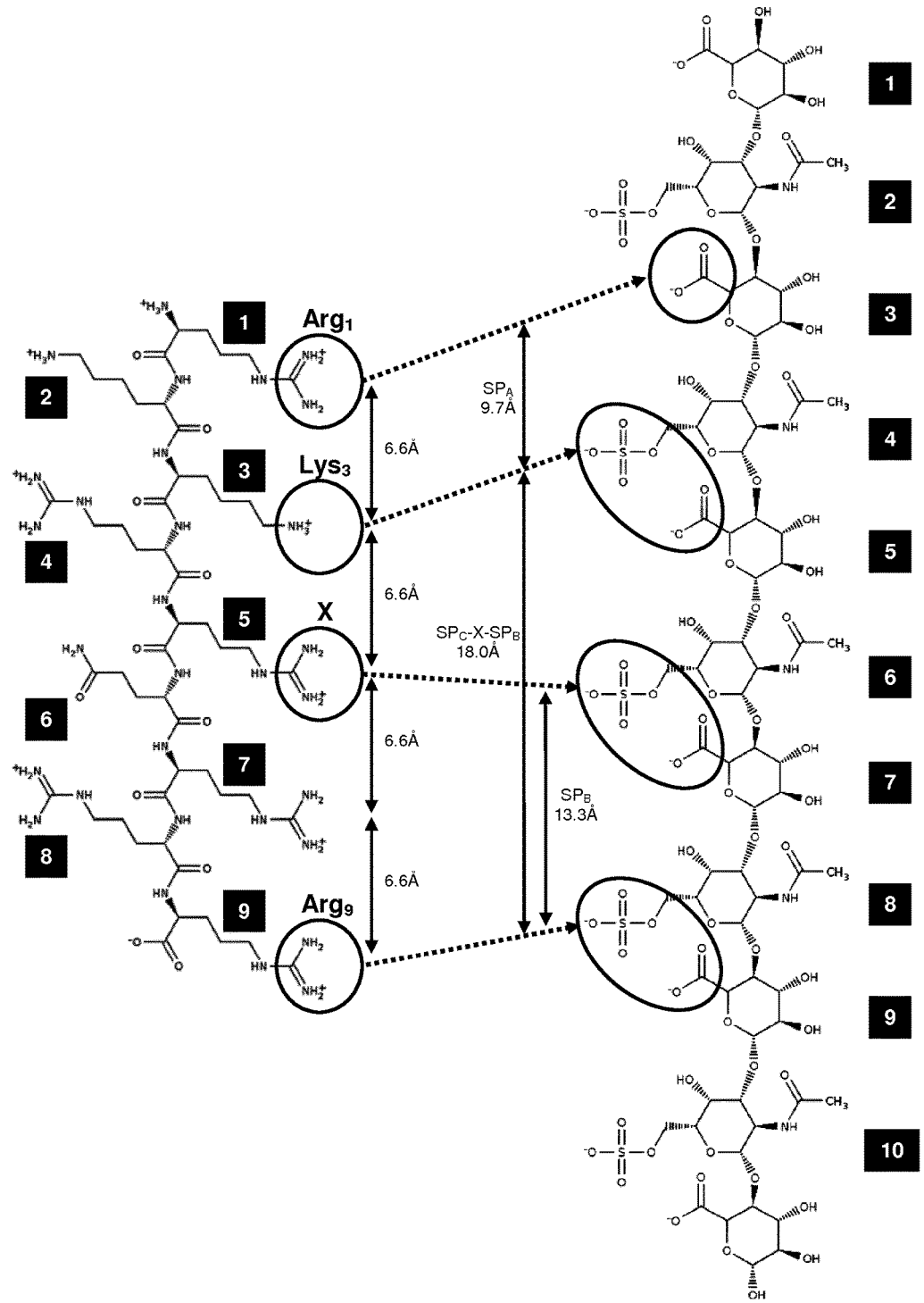

Specification includes a Sequence Listing.

(52) U.S. Cl.
CPC .......... *A61K 47/6455* (2017.08); *A61K 38/00* (2013.01); *C07K 2319/01* (2013.01); *C07K 2319/10* (2013.01); *C07K 2319/20* (2013.01); *C07K 2319/33* (2013.01); *Y02A 50/389* (2018.01); *Y02A 50/401* (2018.01); *Y02A 50/411* (2018.01)

(56) References Cited

OTHER PUBLICATIONS

Butterfield, Karen Chao et al., "Identification and Sequence Composition Characterization of Chondroitin Sulfate-Binding Peptides through Peptide Array Screening," Biochemistry, vol. 49, No. 7, pp. 1549-1555 (Feb. 23, 2010).

Butterfield, Karen Chao et al., "Supplementary Onliine Material—Identification and Sequence Composition Characterization of Chondroitin Sulfate-Binding Peptides through Peptide Array Screening," ACS Publications Biochemistry, pp. 1-43 (Feb. 23, 2010).

De La Fuente-Nunez, C. et al., "Inhibition of Bacterial Biofilm Formation and Swarming Motility by a Small Synthetic Cationic Peptide," Antimicrobial Agents and Chemotherapy, vol. 56, No. 5, pp. 2696-2704 (May 1, 2012).

International Search Report and Written Opinion to corresponding International Application No. PCT/EP2015/059028 dated Jul. 1, 2015.

* cited by examiner

TAT

C6S SPECIFIC TRANSPORTER MOLECULES

The present application is a National Phase application of International Application No. PCT/EP2015/059028, filed Apr. 27, 2015, which claims priority to European Application No. 14165945.8 filed Apr. 25, 2014. The International Application was published in English on Oct. 29, 2015 as Publication No. WO 2015/162285 A1, the entire contents of which are hereby incorporated by reference herein.

1. FIELD OF THE INVENTION

The present invention relates to isolated molecules, peptides, and polypeptides of specific consensus sequences or structures, and to compounds comprising or consisting of such molecules, peptides or polypeptides, that function as transporter moieties or compositions specifically recognizing the proteoglycan, chondroitin 6-sulfate (C6S). The isolated molecules, peptides, polypeptides and compounds of the invention may be conjugated or otherwise linked to a biologically active moiety (BAM). Thus the BAM conjugates allow the specific targeting and delivery of the BAM, which may be, for example, a peptide, chemical entity or nucleic acid, into the cytoplasm and/or nuclei of C6S expressing cells in vitro and in vivo.

2. BACKGROUND OF THE INVENTION

Cellular membranes are generally impermeable to macromolecules, including proteins and nucleic acids. Moreover, even smaller molecules may enter living cells only at very low rates and in the presence of high, potentially toxic extracellular concentrations. The lack of means for specifically targeting and delivering a compound of interest into specific cells or tissues has been an obstacle to the therapeutic, prophylactic and diagnostic or experimental use of a potentially large number of biologically active molecules having intracellular sites of action.

Over the past decade various means for intracellular delivery of compounds have been investigated in an attempt to facilitate efficient transfer of a substance of interest from the external medium into tissues or cells. The most common delivery constructs have been based on antibodies (or antibody fragments) or on viral and bacterial peptides discovered to have membrane binding and transport activity. For example, transporter constructs have been investigated based on herpes viral VP22 protein, polypeptides comprising the human immunodeficiency virus (HIV) TAT protein, and polypeptides comprising a homeodomain of an Antennapedia protein (Antp HD), as well as functional fragments and modifications thereof.

The majority of the viral and bacterial peptides investigated in the delivery constructs (also termed cell-penetrating peptides (CPPs)) comprise cationic peptides rich in basic residues such as lysine and/or arginine, or peptides comprising alpha helix enhancing amino acids. CPPs have been used to transfect cells in vitro in some experimental animal models, but have demonstrated limited success in clinical trials. It has been postulated that the lack of success in the clinic may arise from their lack of specificity for any particular cell type or tissue, as well as the inherent instability of these peptides in vivo (often exhibiting half-lives on the order of several minutes). To circumvent the lack of in vivo stability, several stabilized CPPs have been developed which have been chemically modified to resist standard degradation, for example, by modification to contain non-natural amino acids, including "D" amino-acids. For example, a full "D"-retro-inverso form ("D-TAT") of the archetypal "TAT" peptide has reached clinical Phase 2, but the potentially extremely long persistence of this peptide has limited its uses to topical administration, e.g., to the ear or intraocular for treatment of inflammation of the eye. The systemic administration of such stabilized peptides is contraindicated by virtue of their potential toxicity.

By replacing only specific positions in the "D-TAT" peptide with L-amino acids, peptides have been obtained with an intermediate half-live that are potentially more suitable for clinical development. The transporter constructs disclosed in the applications WO 2010/072406, WO 2010/072228 or WO2010/072275, comprising amino acid sequences with both L- and D-residues exhibit sufficient stability to resist degradation by proteases prior to transport of the cargo moiety to its target site, but do not appear to permanently persist in the cell. Thus, these combination peptides are to some extent subject to protease degradation. Nevertheless, while effective trans-membrane transporter activity has been demonstrated, it has been found that upon uptake, the cargo moiety of the cargo-transporter construct is not readily cleaved from the transporter moiety, which is generally a prerequisite for the cargo moiety to be or become biologically active. Moreover, it has been found that the degradation of the cargo-transporter construct is slow, such that it exhibits the tendency to accumulate in the target cell. Therefore, even if the attached cargo moiety is eventually released or is metabolized, the transporter construct may remain in the cell for a prolonged time and participate in further inter- and intracellular processes leading to unknown and unwanted side effects. Accordingly, there is a need to develop compounds with improved targeting and improved pharmacodynamics for the intracellular delivery of desired cargo moieties.

3. SUMMARY OF THE INVENTION

The inventors have surprisingly discovered that specific consensus sequences of isolated peptides and/or polypeptides are able to effect specific binding to the proteoglycan chondroitin 6-sulfate ("C6S") that are also selective for C6S over other proteoglycans (e.g., heparin, C4S, keratin sulfate ("KS")). Peptides and polypeptides of the invention comprising or consisting of the consensus sequences also exhibit improved in vivo stability relative to similarly sized peptides and, thus, are able to function as improved carrier peptides/peptides for the cellular and intracellular delivery of molecules conjugated to them (e.g., by chemical conjugation or recombinant fusion). The peptides and/or polypeptides according to the invention may consist of or comprise the consensus sequences according to (i) or (ii), or the reverses thereof:

(i)
$Arg_1-X_2-Lys_3-X_4-X_5-X_6-X_7-X_8-Arg_9-(LD_{10})_n-(XD_{11})_m$,
or (ii)
$(XD_{-2})_m-(LD_{-1})_n-Arg_1-X_2-Lys_3-X_4-X_5-X_6-X_7-X_8-Arg_9$ wherein,
(a) $Arg_1$ and $Arg_9$ represent L-arginine; $Lys_3$ represents L-lysine; $LD_{10}$ or $LD_{-1}$ represents any L- or D-amino acid other than D-arginine, D-lysine, L-arginine or L-lysine and n has a value of 0 to 10; $XD_{11}$ or $XD_{-2}$ represents any D-amino acid other than D-arginine or D-lysine and m has a value of 0 or 1; and wherein the remaining amino acids $X_4$ to $X_8$ may be independently selected from any L- or D-amino acid other than D-arginine, D-lysine, L-arginine or L-lysine, with the proviso that either $X_5$ or $X_7$, but not both, represents L-lysine or L-arginine;

or wherein, (b) $Arg_1$ and $Arg_9$ represent D-arginine; $Lys_3$ represents D-lysine; $LD_{10}$ or $LD_{-1}$ represents any L- or D-amino acid other than D-arginine, D-lysine; L-arginine or L-lysine and n has a value of 0 to 10; $XD_{11}$ or $XD_{-2}$ represents any D-amino acid other than D-arginine or D-lysine and m has a value of 0 or 1; and wherein the remaining amino acids $X_4$ to $X_8$ may be independently selected from any L- or D-amino acid other than D-arginine, D-lysine, L-arginine or L-lysine, with the proviso that either $X_5$ or $X_7$, but not both, represents D-lysine or L-arginine;

Consensus sequence (i), above, with conditions (a) is SEQ ID NO:1, and with conditions (b) is SEQ ID NO:2. Consensus sequence (ii), above, with conditions (a) is SEQ ID NO:3, and with conditions (b) is SEQ ID NO:4.

The present inventors have further discovered that, as reflected in the consensus rules above, that the amino acid residues at positions 2, 4, 6, 8 and 7 (where position 5 is defined as the L- or D-lysine or arginine according to the above rules), or 2, 4, 6, 8 and 5 (where position 7 is defined as the L- or D-lysine or arginine according to the above rules)

do not contribute to the binding activity of the peptide. Therefore, the targeting moiety of the above peptide consensus sequences, represented by $Arg_1$-$X_2$-$Lys_3$-$X_4$-$X_5$-$X_6$-$X_7$-$X_8$-$Arg_9$ with the proviso that position $X_5$ or $X_7$ (but not both) is a lysine or arginine (SEQ ID NO:5, where a fragment of SEQ ID NO:1 or SEQ ID NO:3; SEQ ID NO:6, where a fragment of SEQ ID NO:2 or SEQ ID NO:4), can be seen to be to be identical for all possible peptides encompassed by the consensus sequences (i) and (ii), differentiated only in following conditions (a) or (b), above. It is the 3D linear arrangement and/or 3D configuration of side chains of the arginine residues at positions 1 and 9, of the lysine residue at position 3, and of the lysine or arginine residue at position 5 or 7 (but not both) that establishes the binding activity of the targeting moiety sequences and contributes the binding specificity and selectively for C6S relative to other proteoglycans. The remaining amino acid residues, i.e., at positions 2, 4, 6, 8 and 7 (where position 5 is defined as the L- or D-lysine or arginine according to the above rules) or 5 (where position 7 is defined as the L- or D-lysine or arginine according to the above rules), serve primarily as a structural backbone to maintain the proper distance and relative configuration between the arginines at positions 1 and 5, the lysine at positions 3, and the arginine/lysine at position 5 or 7 (but not both) of the targeting moiety. Thus, provided the 3D spatial orientation of these residues is maintained (in particular, the 3D presentation of the amino acid residue side chains), the peptide, polypeptide and/or compositions of the invention will exhibit specific and selective binding for the proteoglycan C6S.

As such, the invention is generally drawn to isolated peptides and polypeptides comprising or consisting of the consensus sequences according to (i) or (ii) above, or to compounds comprising or consisting of such peptides and polypeptides. Further, the invention is also directed to equivalent amino acid residue constructs (or compounds comprising them), which construct is defined as having a 3D presentation of the side chains of 2 arginine residues (i.e., $Arg_1$ and $Arg_9$), the side chain of a lysine residue (i.e., $Lys_3$), and the side chain of a lysine or arginine residue (i.e., the Lys/Arg at position 5 or 7 (but not both)) equivalent to those in the peptides and/or targeting moieties of consensus sequences (i) and (ii). Accordingly, the invention encompasses the use of both amino acid residues in the freely selectable positions (i.e., 2, 4, 6, 8 and 7 (where position 5 is defined as the L- or D-lysine or arginine according to the above rules) or 5 (where position 7 is defined as the L- or D-lysine or arginine according to the above rules)) in the targeting moiety of consensus sequences (i) and (ii)), as well as encompasses the replacement of one or more of these amino acid residues with any appropriate chemical linker or chemical spacer suitable to maintain the equivalent spacing and the relative 3D orientation/presentation of the 2 arginine, 1 lysine, and 1 lysine/arginine residue (i.e., $Arg_1$, $Lys_3$, $Lys/Arg_{5/7}$, and $Arg_9$) of consensus sequences (i) and (ii), in particular, suitable to maintain the equivalent spacing and 3D orientation of their side chains. Therefore, the invention encompasses molecules comprising or consisting of amino acid residues and also encompasses molecules comprising both amino acid residues and chemical linkers/spacers such that the molecules exhibit 2 arginines, 1 lysine and 1 lysine or arginine in the same or an equivalent relative 3-dimensional (3D) confirmation as the arginines at positions 1 and 9, the lysine at position 3, and the arginine or lysine at position 5 or 7 (but not both) as in the targeting moieties of consensus sequences (i) and (ii). As used throughout this disclosure, a molecule comprising the replacement of one or more amino acid residues with a chemical linker/spacer is termed a residue-spacer construct.

For the sake of convenience as used throughout this disclosure, the arginines in the residue-spacer construct that correspond to arginines 1 and 9 of the consensus sequences (i) and (ii) will be referenced as Arg1 and Arg9, respectively. Similarly the lysine in the residue-spacer construct that corresponds to lysine 3 of the consensus sequences (i) and (ii) will be referenced as Lys3. Finally the arginine or lysine that corresponds to the arginine or lysine at position 5 or 7 will be referenced as Arg/Lys5 or Arg/Lys7, respectively; this single residue as it occurs in the consensus sequences or structures between Lys3 and Arg9, generally, is referenced as Arg/Lys(5 or 7).

In view of the foregoing, the invention is generally directed to molecules wherein Arg1 is linked to $Lys_3$ via one or more chemical linkers (which may consist of or comprise an amino acid residue). In embodiments where Arg1 is linked to Lys3 via a chemical linker that is not an amino acid residue, it is preferred that the linker is such that the distance between Arg1 and Lys3 is 9.7±1.5 Å when the molecule/construct is in extended conformation. The invention also encompasses in the same or alternate embodiments molecules wherein Lys3 is linked to Arg9 via one or more chemical linkers (which may consist exclusively of five amino acid residues or may comprise both amino acid residues and chemical spacers/linkers). In embodiments where Lys3 is linked to Arg9 using one or more chemical linkers that is not an amino acid residue, it is preferred that the linker is such that the distance between Lys3 and Arg9 is 18.0±1.5 Å when the molecule/construct is in extended conformation. The molecules of the invention as described by the embodiments in this paragraph further comprise an arginine or lysine residue ("Arg/Lys") within the one or more chemical linkers/spacers between Lys3 and Arg9, wherein (1) Lys3 is linked to the Arg/Lys via three amino acid residues or via one or more chemical linkers/spacers such that the distance between Lys3 and the Arg/Lys is about 13.3±1.5 Å when the molecule/construct is in extended conformation (i.e., to form the construct having the equivalent of an Arg/Lys7 and not an Arg/Lys5); or (2) the Arg/Lys is linked to Arg9 via three amino acid residues or via one or more chemical linkers/spacers such that the distance between the Arg/Lys and Arg9 is about 13.3±1.5 Å when the molecule/construct is in extended conformation (i.e., to form the construct having the equivalent of Arg/Lys5 and not an Arg/Lys7).

Accordingly, the invention encompasses embodiments wherein the linkages between Arg1 and Lys3, between Lys3 and Arg/Lys(5 or 7), and between Arg/Lys(5 or 7) and Arg9 are each independently selected from either (a) amino acid residues (other than D-arginine, D-lysine; L-arginine or L-lysine and according to other rules as outlined herein), or (b) any chemical linker suitable to maintain the relative positions and 3D orientation of the adjoining amino acid residues and their side chains as presented in consensus sequences (i) and/or (ii), above.

Care must be taken when replacing one or more residues with chemical linkers according to the methods described herein so that the side chains of Arg1, Lys3, Arg/Lys(5 or 7) and Arg9 retain the same or similar 3D presentation as their counterpart side chains in the peptide and polypeptides of consensus sequences (i) and (ii). Thus, the side chains of Arg1, Lys3, Arg/Lys(5 or 7) and Arg9 within a residue-spacer construct according to the invention should present a linear or near linear arrangement within 3D space when the molecule/construct is in extended conformation.

With the understanding that $X_2$, $X_4$, $X_6$, $X_8$ and $X_7$ (where $X_5$ is defined as the L- or D-lysine or arginine according to the above rules) or $X_5$ (where $X_7$ is defined as the L- or D-lysine or arginine according to the above rules) of consensus sequences (i) and (ii) may each independently represent either (a) a single D- or L-amino acid residue (other than D-arginine, D-lysine; L-arginine or L-lysine and according to the other selection rules as outlined herein), or (b) one or more chemical linkers, the invention may also be described as directed to at least one isolated molecule, or compounds comprising or consisting of said molecule, wherein the molecule has a consensus structure according to any one of (iii) to (vi), or the reverses thereof:

(iii)
$Arg_1$-$(SP_A)$-$Lys_3$-$(SP_B)$-X-$(SP_C)$-$Arg_9$-$(LD_{10})_n$-$(XD_{11})_m$;

(iv)
$Arg_1$-($SP_A$)-$Lys_3$-($SP_C$)-X-($SP_B$)-$Arg_9$-$(LD_{10})_n$-$(XD_{11})_m$;

(v)
$(XD_{-2})_m$-$(LD_{-1})_n$-$Arg_1$-($SP_A$)-$Lys_3$-($SP_B$)-X-($SP_C$)-$Arg_9$;
or (vi)
$(XD_{-2})_m$-$(LD_{-1})_n$-$Arg_1$-($SP_A$)-$Lys_3$-($SP_C$)-X-($SP_B$)-$Arg_9$;

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein (a) $Arg_1$ and $Arg_9$ represent L-arginine, $Lys_3$ represents L-lysine, and X represents L-arginine or L-lysine;

or (b) $Arg_1$ and $Arg_9$ represent D-arginine, $Lys_3$ represents D-lysine, and X represents D-arginine or D-lysine;

wherein ($SP_A$) represents a chemical linker that (a) consists of a single amino acid residue, which may be any L- or D-amino acid residue other than D-arginine, D-lysine, L-arginine or L-lysine;

or (b) separates the adjacent amino acid residues by 9.7±1.5 Å when the molecule is in extended conformation;

wherein ($SP_B$) represents a chemical linker that (a) consists of a peptide chain of 3 amino acid residues, each of which residues may be independently selected from any L- or D-amino acid residue other than D-arginine, D-lysine, L-arginine or L-lysine;

or (b) separates the adjacent amino acid residues by 13.3±1.5 Å when the molecule is in extended conformation;

and wherein ($SP_C$) represents a chemical linker that (a) consists of a single amino acid residue, which may be any L- or D-amino acid residue other than D-arginine, D-lysine, L-arginine or L-lysine;

or (b) contributes to the linker ($SP_B$)-X-($SP_C$) such that it or its reverse, ($SP_C$)-X-($SP_B$), separates $Lys_3$ and $Arg_9$ by 18.0±1.5 Å when the molecule is in extended conformation.

When replacing one or more amino acid residue with a chemical spacer/linker in the consensus sequence (i) or (ii) (e.g., to form one or more of the molecules (i.e., a residue-spacer construct) according to consensus structures (iii) to (vi)), care must be taken such that the side chains of Arg1, Lys3, Arg/Lys(5 or 7), and Arg9 retain the same or similar 3D presentation as their counterpart side chains in the peptide and polypeptide consensus sequences (i) and/or (ii). Thus, the side chains of Arg1, Lys3, Arg/Lys(5 or 7), and Arg9 within residue-spacer constructs according to the invention should present in a linear or near linear arrangement within 3D space when the molecule and/or construct is in extended conformation.

In certain embodiments the consensus structures (iii) to (vi) according to the invention do not comprise any chemical spacer/linkers, but comprises only amino acid residues. In such embodiments, the invention can be defined as directed to at least one isolated peptide or polypeptide, and/or to compounds comprising or consisting of at least one isolated peptide or polypeptide, which peptide or polypeptide has an amino acid sequence according to the consensus sequence (i) and/or (ii) as defined herein.

In certain embodiments, the consensus structures (iii) to (vi) according to the invention comprise chemical linkers/spacers for $SP_A$, $SP_B$, and $SP_C$ that are not and/or do not comprise amino acid residues. In such embodiments, the invention can be defined as directed to at least one residue-spacer construct, or compounds comprising or consisting of them, wherein the construct has a consensus structure according to any one of (vii) to (x), or the reverses thereof:

(vii)
$Arg_1$-($CL_A$)-$Lys_3$-($CL_B$)-X-($CL_C$)-$Arg_9$-$(LD_{10})_n$-$(Xp_{11})_m$;

(viii)
$Arg_1$-($CL_A$)-$Lys_3$-($CL_C$)-X-($CL_B$)-$Arg_9$-$(LD_{10})_n$-$(XD_{11})_m$;

-continued (ix)
$(XD_{-2})_m$-$(LD_{-1})_n$-$Arg_1$-$(CL_A)$-$Lys_3$-$(CL_B)$-X-$(CL_C)$-$Arg_9$;
or (x)
$(XD_{-2})_m$-$(La_{-1})_n$-$Arg_1$-$(CL_A)$-$Lys_3$-$(CL_C)$-X-$(CL_B)$-$Arg_9$;

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;
wherein
 (a) $Arg_1$ and $Arg_9$ represent L-arginine, $Lys_3$ represents L-lysine, and X represents L-arginine or L-lysine;
 or
 (b) $Arg_1$ and $Arg_9$ represent D-arginine, $Lys_3$ represents D-lysine, and X represents D-arginine or D-lysine;
wherein $(CL_A)$ represents a chemical linker that separates the adjacent amino acid residues by 9.7±1.5 Å when the molecule is in extended conformation;
wherein $(CL_B)$ represents a chemical linker that separates the adjacent amino acid residues by 13.3±1.5 Å when the molecule is in extended conformation;
and wherein $(CL_C)$ represents a chemical linker that contributes to the linker $(CL_B)$-X-$(CL_C)$ such that it or its reverse, $(CL_C)$-X-$(CL_B)$, separates $Lys_3$ and $Arg_9$ by 18.0±1.5 Å when the molecule is in extended conformation.

The molecules and compounds described above according to consensus sequences (iii) to (vi) (including certain embodiments comprising only amino acid residues according to consensus sequences (i) or (ii) and/or comprising chemical linkers and amino acid residues according to consensus structures (vii) to (x)) find particular use as transport and/or targeting moieties in the molecules and compounds described herein, specifically recognizing and/or binding proteoglycans, e.g., as expressed on the surface of a cell. In particular, the molecules and compounds as described herein bind the proteoglycan C6S specifically and selectively over other proteoglycans. The portion of the above consensus sequences (iii) to (vi) acting as the targeting moiety that specifically interacts with the C6S proteoglycan is represented by $Arg_1$-$(SP_A)$-$Lys_3$-$(SP_B)$-X-$(SP_C)$-$Arg_9$,
or $Arg_1$-$(SP_A)$-$Lys_3$-$(SP_C)$-X-$(SP_B)$-$Arg_9$.

These targeting moieties include the specific embodiments comprising only amino acid residues, i.e., $Arg_1$-$X_2$-$Lys_3$-$X_4$-$X_5$-$X_6$-$X_7$-$X_8$-$Arg_9$ (SEQ ID NO:5, where a fragment of SEQ ID NO:1 or SEQ ID NO:3; or SEQ ID NO:6, where a fragment of SEQ ID NO:2 or SEQ ID NO:4). These targeting moieties also include the specific embodiments wherein the freely selectable positions are replaced by chemical linkers/spacers, i.e., $Arg_1$-$(CL_A)$-$Lys_3$-$(CL_B)$-X-$(CL_C)$-$Arg_9$ or $Arg_1$-$(CL_A)$-$Lys_3$-$(CL_C)$-X-$(CL_B)$-$Arg_9$. As explained herein, these targeting moieties are identical molecules with respect to the 3D presentation of the amino acid residues corresponding to Arg1, Lys3, X (i.e., Arg/Lys(5 or 7)), and Arg9, in particular, the sides chains of these residues. Accordingly, any molecule comprising 2 arginine residues, 1 lysine residue, and 1 arginine or lysine residue according to consensus sequences (iii) to (vi) can be developed as the targeting moiety according to the following rules:

(1) Each of the residues Arg1, Lys3, and Arg9 must have the same chirality, i.e., each must be an L-amino acid or each must be a D-amino acid.
(2) Arg1 must be linked to Lys3 using a chemical spacer, which spacer may be either (a) any L- or D-amino acid other than D-arginine, D-lysine; L-arginine or L-lysine; or (b) a chemical spacer that separates the amino acids by 9.7±1.5 Å when the molecule is in an extended conformation.
(3) Lys3 must be linked to Arg9 using one or more chemical spacers, which spacer may either
 (a) consist exclusively of a peptide chain of 5 amino acid residues having a single arginine or lysine residue that has the same chirality as Arg1, Lys3 and Arg9, and having the remaining 4 residues independently selected from any L- or D-amino acid other than D-arginine, D-lysine; L-arginine or L-lysine; or
 (b) comprise at least one amino acid residue and one or more chemical linkers such that Lys3 and Arg9 are separated by 18.0±1.5 Å when the molecule is in an extended conformation, wherein, if more than one amino acid residue is present, only one amino acid residue is an arginine or lysine having the same chirality as Arg1, Lys3 and Arg9, and any remaining residue(s) is(are) independently selected from any L- or D-amino acid other than D-arginine, D-lysine; L-arginine or L-lysine.
(4) The single arginine or lysine residue in the spacer defined according to rule (3)(a) or (b) (i.e., in the spacer linking Lys3 and Arg9) corresponds to $X_5$ or $X_7$ in consensus sequences (i) or (ii) and/or to X in consensus sequences (iii) to (vi). This Arg/Lys residue (i.e., Arg/Lys(5 or 7) as defined herein) is positioned within the spacer construct according to rule (3) above such that (a) it is separated from either Lys3 or Arg9 by a peptide chain consisting of 3 amino acid residues that are independently selected from any L- or D-amino acids other than D-arginine, D-lysine; L-arginine or L-lysine; or (b) it is separated from either Lys3 or Arg9 by 13.3±1.5 Å when the molecule is in an extended conformation.
(5) Where one or more of the linkages between Arg1 and Lys3, between Lys3 and Arg/Lys(5 or 7), and between Arg/Lys(5 or 7) and Arg9 are not exclusively amino acid residues, i.e., are chemical spacers/linkers or residue-spacer constructs (i.e., comprising both amino acids and chemical linkers), they may comprise any chemical spacer or linker known in the art and/or described herein suitable for maintaining the required separation between Arg1 and Lys3, between Lys3 and Arg/Lys(5 or 7), or between Arg/Lys(5 or 7) and Arg9 as well as suitable to maintain a 3D orientation and/or 3/D presentation of these amino acids (in particular, their side chains) similar to or the same as that in the corresponding residues in consensus sequences (i) and (ii). The linkages between Arg1 and Lys3, between Lys3 and Arg/Lys(5 or 7), and between Arg/Lys(5 or 7) and Arg9 should preferentially not be positively charged.

For all molecules and compounds of the invention, i.e., comprising or consisting of any of consensus sequences (iii) to (vi) (including embodiments according to consensus sequences (i), (ii), and (vii) to (x)) it is further preferred, but not necessary, that $LD_{10}$ or $LD_{-1}$, represents L- or D-histidine and that $XD_{11}$ or $XD_{-2}$ represents D-histidine.

As explained throughout this description, Arg/Lys(5 or 7) is the single arginine or lysine residue in the spacer linking Lys3 and Arg9 and is defined according to the selection rules defined herein. Where the molecules and compounds are designed/selected such that this single Arg/Lys residue is to correspond to position 7 of consensus sequences (i) or (ii) (and, thus, not position 5 thereof, i.e., to correspond to X of consensus sequences (iii), (v), (vii) and/or (ix)), it is preferred, but not required that the residue is an L-lysine residue (where Arg1, Lys3 and Arg9 are L-amino acids) or a D-lysine residue (where Arg1, Lys3 and Arg9 are D-amino acids).

Where the consensus structures of the invention consist of or comprise exclusively amino acids (i.e., correspond to consensus sequences (i) or (ii) and wherein ($SP_A$), ($SP_B$) and ($SP_C$) according to consensus sequences (iii) to (vi) comprise exclusively amino acids), it is preferred, but not necessary, that the structures do not comprise or consist entirely of amino acid residues having a single chirality. That is, it is preferred, but not necessary that where the consensus structures of the invention consist of or comprise exclusively amino acid residues, the molecules or compounds of the invention comprise at least one L-amino acid residue and at least one D-amino acid residue within their consensus sequences, i.e., that ($SP_A$), ($SP_B$) and ($SP_C$) together comprise at least one L-amino acid and one D-amino acid. As a non-limiting exemplary embodiment, it is preferred, but not required that where Arg1, Lys3, Arg/Lys(5 or 7) and Arg9 are L-amino acids that the at least one D-amino acid is present at position 4 or position 6, i.e., at $X_4$ or $X_6$. In related or separate embodiments and subject to the other rules outlined herein, it is further preferred that the freely selectable positions, i.e., $X_2$, $X_4$, $X_6$, $X_8$ and $X_7$ (where $X_5$ is defined as the L- or D-lysine or arginine according to the above rules) or $X_5$ (where $X_7$ is defined as the L- or D-lysine or arginine according to the above rules), are each independently selected from the amino acids isoleucine, tyrosine, phenylalanine, tryptophan, valine, methionine, and leucine. It is also preferred that in related or separate embodiments of the invention directed to consensus sequences (i) or (ii), the consensus sequences do not comprise more than 3 alanine residues and/or that the freely selectable positions together do not comprise more than 3 alanine residues. It is also preferred that in related or separate embodiments of the invention directed to consensus sequences (i) or (ii), the consensus sequences do not comprise proline and/or that the freely selectable positions do not comprise proline.

Where the consensus structures of the invention consist of or comprise residue spacer constructs (i.e., wherein ($SP_A$), ($SP_B$) and ($SP_C$) according to consensus sequences (iii) to (vi) together comprise both amino acid residues and chemical linkers according to the rules set forth herein), it is preferred, but not necessary, that, if an amino acid is present at a position corresponding to $X_4$ or $X_6$ of consensus sequences (i) and/or (ii), it is a D-amino acid. In a non-limiting example of this embodiment, where ($SP_B$) consists of a peptide chain of 3 amino acids, it is preferred, but not necessary, that the first amino acid of the chain is a D amino acid. In related or separate embodiments and subject to the other rules outlined herein, it is also preferred that any amino acids present in ($SP_A$), ($SP_B$) and ($SP_C$) (if present) are each independently selected from the amino acids isoleucine, tyrosine, phenylalanine, tryptophan, valine, methionine, and leucine. In related or separate embodiments and subject to the other rules outlined herein, it is also preferred that ($SP_A$), ($SP_B$) and ($SP_C$) together comprise no more than 3 alanine residues. In related or separate embodiments and subject to the other rules outlined herein, it is also preferred that ($SP_A$), ($SP_B$) and ($SP_C$) together comprise no proline residues.

Non-limiting examples of peptides that may be used according to the methods disclosed herein and, in particular, as defined hereinabove are provided in Table 1.

TABLE 1

| Exemplary Peptides Of The Invention* |
| --- |
| RYKvFIKYR (SEQ ID NO: 7) |
| RYKvFIKYRh (SEQ ID NO: 8) |
| RYKvAIKYR (SEQ ID NO: 9) |
| RYKvAIKYRh (SEQ ID NO: 10) |
| RYKvRIAYR (SEQ ID NO: 11) |
| RYKvRIAYRh (SEQ ID NO: 12) |
| RYKvRIFYR (SEQ ID NO: 13) |
| RYKvRIFYRh (SEQ ID NO: 14) |
| RYKvKFIYR (SEQ ID NO: 15) |
| RYKvKFIYRh (SEQ ID NO: 16) |
| RYKvFIRYR (SEQ ID NO: 17) |
| RYKvFIRYRh (SEQ ID NO: 18) |
| RYKvRFIYR (SEQ ID NO: 19) |
| RYKvRFIYRh (SEQ ID NO: 20) |
| RMKiVMKFR (SEQ ID NO: 21) |
| RMKiVMKFRh (SEQ ID NO: 22) |
| RFKfFFKFR (SEQ ID NO: 23) |
| RFKfFFKFRh (SEQ ID NO: 24) |

*lower case indicates D-enantiomer; upper case indicates L-enantiomer

In addition to the peptides, polypeptides and compounds comprising or consisting of the molecules according to the consensus sequences (i) or (ii), the invention further encompasses variants of the exemplary peptide sequences explicitly disclosed herein. Such variants comprise substitution of the amino acid residues corresponding to the freely selectable positions, i.e., corresponding to $X_2$, $X_4$, $X_6$, $X_8$ and $X_7$ (where $X_5$ is defined as the L- or D-lysine or arginine according to the above rules) or $X_5$ (where $X_7$ is defined as the L- or D-lysine or arginine according to the above rules) in consensus sequences (i) and (ii), e.g., with a conservative amino acid substitution. As is well known in the art, "conservative substitutions" are substitutions with another amino acid having similar characteristics, e.g., small amino acids substituted for small amino acids, acidic amino acids substituted for acidic amino acids, etc. As known in the art, this principle may be applied to any characteristic class of amino acids e.g., polar amino acids, basic amino acids, hydrophobic amino acids and aromatic amino acids. Preferred substitutions for a particular residue according to the present invention may be chosen from among the other members of its conservative substitution group. Six conservative substitution groups are commonly recognized in the art: (1) alanine (A), glycine (G) serine (S) and threonine (T); (2) aspartic acid (D) and glutamic acid (E); (3) asparagine (N) and glutamine (Q); (4) arginine (R), histidine (H) and lysine (K); (5) isoleucine (I), leucine (L), methionine (M) and valine (V); and (6) phenylalanine (F), tyrosine (Y) and tryptophan (W).

However, the substitutions of one or more amino acid residues corresponding to the freely selectable positions, e.g., in consensus sequences (i) and (ii), need not be made with a member of its conservative substitution group. The invention also contemplates the substitution of any residue at these positions with any other L- or D-amino acid other than L- or D-arginine or L- or D-lysine subject to the rules of the consensus sequences outlined herein. Again, as has been detailed herein, the residues at the positions corresponding to $X_2$, $X_4$, $X_6$, $X_8$ and $X_7$ (where $X_5$ is defined as the L- or D-lysine or arginine according to the above rules) or $X_5$ (where $X_7$ is defined as the L- or D-lysine or arginine according to the above rules) of consensus sequences (i) and (ii) do not substantially contribute to targeting effects.

In all embodiments of the invention, use of the amino acid proline (P) in any consensus sequences (i) to (vi), e.g., in any of the residue-spacer construct defined therein, should be avoided as this residue would destroy or sufficiently distort the 3-dimensional conformation of the molecule or peptide so as to significantly reduce binding activity or affinity.

Any appropriate chemical linker or chemical spacer suitable to maintain the spacing and the relative 3D orientation/presentation of the 2 arginine, 1 lysine residue and 1 Arg/Lys residue (i.e., corresponding to Arg1, Arg9, Lys3 and Arg/Lys(5 or 7)) and their side chains equivalent to the corresponding residues in consensus sequences (i) and (ii) known in the art or described herein may be used in the construction of the molecules of the invention according to consensus structures (iii) to (x). Nonlimiting examples of appropriate chemical linkers/spacers include beta- and gamma-peptides; sugar amino acid based scaffolds; beta-hairpin peptidometics; alpha-helical mimetic, beta-sheet/beta-stand mimetics and beta-turn mimetics and cyclotides. In preferred embodiments, the chemical linker/spacers are not positively charged. The linkers should be subject to metabolic breakdown, non-toxic (including metabolites) and should not significantly reduce the solubility of the compounds of the invention.

It is expressly contemplated that the embodiments described throughout this application, whether identified as preferred (including most preferred) or not, can be independently implemented and/or can be combined with the other disclosed embodiments in the design or selection of a peptide of the invention. Therefore, a sequence or structure of the targeting moiety of the peptide, polypeptide, molecule or compound of the invention must satisfy the rules (1) to (5) listed above, and may optionally satisfy none, one, or more than one of the conditions outlined in the other embodiments disclosed herein whether preferred or not.

The invention may comprise the isolated molecules and compounds (including isolated molecules, peptides, polypeptides and compounds comprising or consisting of the molecules, peptides and/or polypeptides) according to consensus sequences (iii) or (vi) (including embodiments according to consensus sequences (i) and (ii) and consensus structures (vii) to (x)) and may further comprise a biologically active moiety (BAM; also referenced as the "cargo" of the targeting moiety). The (BAM)-(targeting moiety) construct may also be referenced as a BAM-conjugate of the invention throughout the disclosure. The BAM may be chemically conjugated to the compounds, peptides, polypeptides and/or molecules of the invention directly and/or may be linked thereto through a linker group.

As used throughout the disclosure, direct conjugation indicates the conjugation of the BAM moiety to any amino acid residue within consensus sequences (iii) to (vi) (including embodiments according to consensus sequences (i) and (ii) and consensus structures (vii) to (x)), or to any amino acid residue or suitable chemical group therein, using any chemical coupling known in the art or described herein suitable for the conjugation of the BAM moiety to an amino acid residue (e.g., an amino acid side chain) and/or chemical group. Accordingly, direct coupling may result in one or more chemical groups spaced between the BAM moiety and the amino acid (e.g., amino acid side chain) or between the BAM moiety and the chemical group of the residue-spacer construct, which groups form as a result of the coupling reaction as is known in the art.

Alternatively, as described herein, the BAM moiety may be conjugated to any amino acid residue or chemical group within consensus sequences (iii) to (vi) (including embodiments according to consensus sequences (i) and (ii) and consensus structures (vii) to (x)), indirectly, that is, via a linker group. Therefore, as used throughout this disclosure, indirect conjugation means that the BAM is conjugated to the linker group, which linker group is conjugated to an amino acid residue or chemical group within a consensus sequence as defined herein. The conjugation between the BAM and the linker group and between the linker group and an amino acid residue or chemical group of a residue spacer construct or molecule of the invention may be any conjugation method and/or compound suitable for effecting such conjugation as described herein or as is otherwise known in the art.

The direct or indirect conjugation of the BAM moiety may be directed to any amino acid residue or chemical linker/spacer group within the molecules of the invention. Thus, the BAM moiety may be directly or indirectly conjugated to an amino acid residue that is at the N or C terminus of consensus sequence (iii) to (vi) (including embodiments according to consensus sequences (i) and (ii) and consensus structures (vii) to (x)). Alternatively or additionally, the BAM moiety may be directly or indirectly conjugated to an internal amino acid residue or chemical linker/spacer group within molecules of the invention. As used throughout this disclosure, an internal residue or internal chemical group references an amino acid residue or chemical group of consensus sequence (iii) to (vi) that is not at the terminus of the linear peptide chain or linear residue-spacer construct. As is known in the art, conjugation methods (whether direct or indirect) may require the chemical modification of one or both sites of conjugation (e.g., modification of an amino acid residue, modification of a chemical group within the molecule of the invention and/or modification of the BAM moiety). Accordingly, the present invention also encompasses chemical modification of the molecules of the invention, compounds comprising or consisting of the molecules, and/or conjugate components.

The compounds and molecules of the invention may also comprise or consist of a peptide, small molecule or other moiety conjugated to a molecule of the invention wherein the peptide, small molecule or other moiety has a desired biological activity, i.e., is a biologically active moiety ("BAM"). The invention encompasses the use of any BAM known in the art or described herein in any form, e.g., peptide, small molecule or other, provided that the BAM has a desired activity and/or recognized therapeutic effect. Therefore, the compounds of the invention may comprise or consist of peptide or non-peptide BAMs conjugated to molecules and/or compounds of the invention by any means known in the art or described herein. In certain embodiments, the BAM-conjugates of the invention have a BAM conjugated at the terminus of a consensus sequence or structure (i) to (x) as described herein. Therefore, in these preferred embodiments, the BAM-conjugate has a structure according to the following consensus structures (xi) to (xiv), or the reverses thereof:

(xi)
(BAM)-(LINK)-$Arg_1$-($SP_A$)-$Lys_3$-($SP_B$)-X-($SP_C$)-$Arg_9$-($LD_{10}$)$_n$-($XD_{11}$)$_m$;

(xii)
(BAM)-(LINK)-$Arg_1$-($SP_A$)-$Lys_3$-($SP_C$)-X-($SP_B$)-$Arg_9$-($LD_{10}$)$_n$-($XD_{11}$)$_m$;

(xiii)
($XD_{-2}$)$_m$-($LD_{-1}$)$_n$-$Arg_1$-($SP_A$)-$Lys_3$-($SP_B$)-X-($SP_C$)-$Arg_9$-(LINK)-(BAM);

(xiv)
($XD_{-2}$)$_m$-($LD_{-1}$)$_n$-$Arg_1$-($SP_A$)-$Lys_3$-($SP_C$)-X-($SP_B$)-$Arg_9$-(LINK)-(BAM);

wherein (BAM) represents a biologically active moiety; wherein (LINK) represents an optional linker group; wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;
wherein
  (a) $Arg_1$ and $Arg_9$ represent L-arginine, $Lys_3$ represents L-lysine, and X represents L-arginine or L-lysine; or
  (b) $Arg_1$ and $Arg_9$ represent D-arginine, $Lys_3$ represents D-lysine, and X represents D-arginine or D-lysine;
wherein ($SP_A$) represents a chemical linker that
  (a) consists of a single amino acid residue, which may be any L- or D-amino acid residue other than D-arginine, D-lysine, L-arginine or L-lysine; or
  (b) separates the adjacent amino acid residues by 9.7±1.5 Å when the molecule is in extended conformation;
wherein ($SP_B$) represents a chemical linker that
  (a) consists of a peptide chain of 3 amino acid residues, which may be independently selected from any L- or D-amino acid residue other than D-arginine, D-lysine, L-arginine or L-lysine; or
  (b) separates the adjacent amino acid residues by 13.3±1.5 Å when the molecule is in extended conformation;
and wherein ($SP_C$) represents a chemical linker that
  (a) consists of a single amino acid residue, which may be any L- or D-amino acid residue other than D-arginine, D-lysine, L-arginine or L-lysine; or
  (b) contributes to the linker ($SP_B$)-X-($SP_C$) such that it or its reverse, ($SP_C$)-X-($SP_B$), separates $Lys_3$ and $Arg_9$ by 18.0±1.5 Å when the molecule is in extended conformation.

Consensus sequences (xi) to (xiv) are identical to consensus sequences (iii) to (vi), respectively, but for the presence of the BAM-moiety and the optional linker group, (LINK). Therefore, selection of the chemical spacers ($SP_A$), ($SP_B$) and ($SP_C$), which may consist of one or more amino acid residues, one or more chemical linkers or comprise both amino acid residues and chemical linkers, proceeds as disclosed herein with respect to consensus sequences (iii) to (vi), including
  selection of these chemical spacers to consist of or comprise exclusively amino acid residues according to the embodiments (and combinations thereof) of consensus sequences (i) and (ii) as detailed throughout this disclosure, and
  selection of these chemical spacers to comprise chemical linkers or to comprise both amino acid residues and chemical linkers according to the embodiments (and combinations thereof) of consensus structures (iii) to (x) as detailed throughout this disclosure.

Where a linker group is present, (e.g., (LINK) in consensus structures (xi) to (xiv)) and/or a linker group used in the indirect linkage of the BAM to an amino acid residue or to a chemical group in any of consensus sequences/structures (i) to (x), such linker may be any linker, e.g., a peptide linker, known in the art or disclosed herein suitable for linking the BAM to the remaining targeting moiety. The BAM may be chemically conjugated to the linking group. For example, where both the linking group, (e.g., (LINK) of structures (xi) to (xiv)), and the BAM are peptides or polypeptides, the BAM may be linked to the linking group via a peptide bond and the linking group may also be linked to the targeting moiety of the consensus sequence/structure via a peptide bond. Non-limiting examples of linker groups include peptide linkers, e.g., comprising one or more residues of glutamic acid, glycine, serine, cysteine and combinations thereof. In certain embodiments, the linking group (LINK) of structures (xi) to (xiv) is a single amino acid that is L- or D-glutamic acid.

The invention also encompasses molecules and compounds comprising or consisting of the molecules, e.g., peptide-conjugates/residue-spacer-conjugates/BAM-conjugates, that do not comprise a linking group, i.e., wherein consensus structures (vi) to (xiv) lack the (LINK) moiety and/or comprise direct linkage of the BAM moiety to any amino acid residue or chemical group within any consensus sequence/structure (i) to (x). Where the BAM-conjugate of the invention is lacking the linking group, the BAM may be conjugated, e.g., chemically conjugated, directly to the molecules' amino acid residue or chemical group (e.g., a chemical group of the chemical linker/spacer). Non-limiting examples of such chemical conjugation include covalent attachment to the molecule at the N-terminus and/or to the N-terminal amino acid residue via an amide bond or at the C-terminus and/or C-terminal amino acid residue via an ester bond. Where the BAM is a peptide or polypeptide, the BAM may be directly conjugated to the N-terminus and/or N-terminal amino acid or to the C-terminus and/or C-terminal amino acid via a peptide bond.

The invention encompasses any BAM expected to exert a therapeutically relevant activity on administration to an organism or on delivery to one or more cells of an organism, whether in vitro or in vivo. Accordingly, non-limiting examples of BAMs encompassed by the invention include mono- and poly-saccharides, cytotoxic agents, antineoplastic agents, anti-inflammatory agents, anti-viral agents, anti-bacterial agents, and agents for the treatment of protozoan infections. The BAM may also be a deoxyribose or ribose.

Non-limiting examples of anti-neoplastic agents that may be used as BAMs according to the methods of the invention include, but are not limited to, aldesleukin, alemtuzumab, alitretinoin, allopurinol, altretamine, amifostine, anastrozole, abiraterone, arsenic, axitinib, azacitidine, bendamustine, bexarotene, bleomycin, bortezomib, busulfan, cabazitaxel, calusterone, capecitabine, carboplatin, carfilzomib, carmustine, carmustine, celecoxib, chlorambucil, cisplatin, cladribine, clofarabine, crizotinib, cyclophosphamide, cytarabine, dacarbazine, dactinomycin, actinomycin D, dasatinib, daunorubicin, decitabine, dexrazoxane, docetaxel, doxorubicin, entinostat, epirubicin, eribulin, erlotinib, estramustine, etoposide, everolimus, exemestane, fostamatinib, floxuridine, fludarabine, fluorouracil, 5-FU, fulvestrant, gefitinib, gemcitabine, hydroxyurea, idarubicin, lenalidomide, ifosfamide, imatinib, iomustine, irinotecan, isotretinoin, ixabepilone, lapatinib, lenalidomide, letrozole, leucovorin, levamisole, lomustine, CCNU, marizomib, meclorethamine, nitrogen mustard, melphalan, L-PAM, mercaptopurine, 6-MP, mertansine, mesna, methotrexate, methoxsalen, mitomycin, mitotane, mitoxantrone, nandrolone, nelarabine, nilotinib, oxaliplatin, paclitaxel, pamidronate, pazopanib, pegademase, pemetrexed, pentostatin, pipobroman, plerixafor, plicamycin, mithramycin, porfimer, pralatrexate, procarbazine, quinacrine, rapamycin, romidepsin, ruxolitinib, sorafenib, streptozocin, sunitinib, tamoxifen, temozolomide, temsirolimus, teniposide, VM-26, testolactone, thalidomide, thioguanine, 6-TG, thiotepa, topotecan, toremifene, tretinoin, ATRA, uracil mustard, valrubicin, vandetanib, vemurafenib, verteporfin, vinblastine, vincristine, vinorelbine, vismodegib, vorinostat, zoledronate, nucleoside analogues AZT, b-D-arabinofuranose, vidarabine, 2-chlorodeoxyadenosine, intercalating drugs, kinase inhibitors, cofarabine, laromustine, clophosphamide, asparaginase, dexamethasone, prednisone and lestaurtinib. The above-listed anti-neoplastic agents may be used in accordance with the methods disclosed herein not only in connection with neoplastic diseases, but also in the treatment, prevention and/or amelioration of other diseases, or symptoms thereof, as is known in the art, e.g., in connection with the treatment, prevention and/or amelioration of anti-inflamatory or autoimmune diseases, and/or symptoms thereof.

Examples of anti-inflammatory agents that may be used as BAMs according to the methods of the invention include, but are not limited to, COX-2 inhibitors, prednisone, pazopanib, famotidine, dalfampridine, pegloticase, esomeprazole, aspirin, celecoxib, diclofenac, valdecoxib, rofecoxib, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, sulindac, tolmetin, lansoprazole, meclofenamate, triamcinolone, methylprednisolone, betamethasone, budesonide, prednisolone, hydrocortisone, dexamethasone and cortisone.

Examples of anti-protozoal agents that may be used as BAMs according to the methods of the invention include, but are not limited to, chloroquine, mefloquine, primaquine, proguanil hydrochloride, proguanil hydrochloride with atovaquone, pyrimethamine, sulfadoxine, quinine, quinoline, doxycycline, clindamycin, artesunate, diloxanide, metronidazole, tinidazole, mepacrine hydrochloride, amphotericin, pentamidine, pyrimethamine, sulfadiazine, azithromycin, atovaquone, trimethoprim-sulphamethoxazole, trimethoprim, dapsone, atovaquone, pentamidine isetionate, amodiaquine, chloroguanide, eflornithine, hydroxychloroquine, iodoquinol, meglumine antimonate, melarsoprol, nifurtimox, paromomycin, sodium stibogluconate, suramin, and tryparsamide.

As detailed herein, the compounds of the invention comprise or consist of a BAM-conjugate (i.e., a BAM conjugated to the targeting moiety; also referenced as a peptide-conjugate) that may effect intracellular transport of the BAM. Accordingly, in preferred embodiments, the invention encompasses a pharmaceutical composition comprising a compound of the invention, e.g., a BAM-conjugate, and a pharmaceutically acceptable carrier. The pharmaceutical compositions of the invention comprising, e.g., the BAM-conjugate, may be used for any indication known or predicted to be treatable with the BAM. For example, where the BAM is an anti-viral agent, the pharmaceutical composition comprising the BAM conjugate may be used in the treatment of a viral infection, or a symptom thereof, including but not limited to HIV; Epstein Barr virus; morbillivirus; paramyxovirus; rubivirus; herpes virus; dengue virus; herpes simplex virus; parvovirus; respiratory syncytial virus; variola virus; varicella; flavivirus; human T-lymphotropic virus; hepatitis virus A, B, C, D or E, lassa virus and/or influenza virus. Where the BAM is an anti-protozoal agent, the pharmaceutical composition comprising the BAM-conjugate may be used in the treatment of protozoal infections, such as leshmaniasis and/or malaria.

The targeting moieties of consensus sequences/structures (i) to (xiv) interact specifically with proteoglycans, in particular, chondroitin 6-sulfate (C6S). C6S is preferentially expressed relative to other proteoglycans, by certain tissues, for example, tissues of the central nervous system, heart, ovary and testis. Accordingly, the invention encompasses the use of the molecules and compounds, e.g., BAM-conjugates, to specifically target cells expressing C6S. The invention also encompasses the use of the molecules and compounds, e.g., BAM-conjugates, to facilitate transport of the BAM moiety into cells expressing C6S.

The molecules and compounds of the invention (including isolated molecules peptides, polypeptides and compounds comprising or consisting of any of consensus sequences (i) to (xiv)) may find particular use in the treatment of C6S and KS accumulation diseases such as morquio syndrome. The molecules and compounds of the invention may also find particular use in the targeting of cells of the central nervous system, heart, ovary and testis. Thus, the molecules of the invention may find particular use in the treatment, prevention or amelioration of symptoms associated with diseases or conditions in which these cells are pathophysiologically involved or have pathophysiological involvement. For example, nonlimiting examples of diseases or conditions affecting heart tissue that may be treated using the molecules and compound of the invention include angina, arrhythmia, atrial fibrillation, dilated cardiomyopathy, hypertrhophic cardiomiopahthy, congestive heart failure, endocarditis, heart rhythm disorders, myocarditis, pericarditis, premature ventricular contractions, and Wolff-Parkinson-White syndrome.

The molecules and compounds of the invention (including isolated molecules peptides, polypeptides and compounds comprising or consisting of any of consensus sequences (i) to (xiv)) may find particular use in the treatment of diseases and conditions involving tissues of the ovary or testis. Non-limiting examples of such diseases and conditions affecting the ovary or testis that may be treated using the molecules and compounds of the invention include epididymitis, orchitis, spermatocele, varicocele, male hypogonadism, testicular cancer, infertility, ovarian cyst, polycystic ovary syndrome, premature ovarian failure, and ovarian cancer.

The molecules and compounds of the invention (including isolated molecules peptides, polypeptides and compounds comprising or consisting of any of consensus sequences (i) to (viii)) find particular use in the targeting of cells of the central nervous system. Thus, the molecules of the invention may find particular use in the treatment, prevention or amelioration of symptoms associated with diseases or conditions affecting such cells, e.g., glial cells. Nonlimiting examples of such diseases or conditions affecting the central nervous system that may be treated using the molecules and compound of the invention include glial-related conditions of the central nervous system, anxiety disorders, depression, epilepsy, spinal muscular atrophy, amyotrophic lateral sclerosis, Alzheimer's disease, autism, Ataxia Telangiectasia, Niemann Pick disease Type C, cerebellar degeneration, Machado-Joseph Disease, olivopontocerebella atrophy, spinocerebella ataxias, sporadic ataxia, multiple system Atrophyatrophy, Parkinson's disease, Parkison's syndrome, gait ataxia, herpes zoster, viral encephalitis, Japanese encephalitis, bacterial encephalitis, toxoplasmosis, malaria, amoebic meningoencephalitis, *Cryptococcus neoformans* encephalitis, Lyme disease, streptococci meningoencephalitis, staphylococci meningoencephalitis, astrocytoma, glioblastoma, oligodendroglioma, ependymoma, medulloblastoma and meningioma.

4. DEFINITIONS

The term "chemical derivatives" as used herein refers to the (chemical) modification of amino acids, amino acid side chains and peptide bonds (including those at the N-terminus, at the C-terminus, and within the backbone of the consensus structure/sequence) as well as modification of any chemical group within the chemical spacer/linker of consensus structures (iii) to (xiv). The term is not intended to refer to any addition, substitution or deletion of amino acids residues in an amino acid or peptide chain. Chemical derivatives from L-amino acids or L-enantiomeric amino acids typically comprise any naturally or non-naturally occurring derivative of these amino acids, including, without being limited thereto, amino acids as defined above comprising post-translational modifications or synthetic modifications, including acetylation (at the N-terminus of the (poly-)peptide sequence, at lysine residues, etc.), deacetylation, alkylation (such as methylation, ethylation, etc. (preferably at lysine or arginine residues within the (poly-)peptide sequence)), dealkylation (such as demethylation, deethylation, etc., amidation (preferably at the C-terminus of the (poly-)peptide sequence)), formylation, gamma-carboxylation, glutamylation, glycosylation (preferably at asparagine, lysine, hydroxylysine, serine or threonine residues, etc., within the (poly-)peptide sequence), addition of a heme or haem moiety, hydroxylation, iodination, isoprenylation addition of an isoprenoid moiety such as farnesyl or geranylgeraniol, etc.), lipoylation (attachment of lipoate functionality), such as prenylation, formation of a GPI anchor, including myristoylation, farnesylation, geranylgernaylation, etc., oxidation, phosphorylation (e.g. to a serine, tyrosine, threonine or a histidine moiety, etc., within the (poly-)peptide sequence), sulfation (e.g., of tyrosine), selenoylation, etc. Chemical derivatives of amino acids also include, without being limited thereto, modified amino acids, which have been modified by introducing a label, including radioactive labels, a dye or fluorescent group, or a chemoluminesent group.

As used herein, the term "freely selectable positions", "freely selectable amino acids" and analogous terms reference the amino acid residues (if present) at the positions corresponding to those positions in consensus sequences (i) and (ii) that are not explicitly defined. The targeting moiety of consensus sequences (i) and (ii) is represented by $Arg_1$-$X_2$-$Lys_3$-$X_4$-$X_5$-$X_6$-$X_7$-$X_8$-$Arg_9$, wherein $Arg_1$ and $Arg_9$ represent D-or L-arginine (each of the same chirality), $Lys_3$ represents D- or L-lysine (having the same chirality as $Arg_1$ and $Arg_9$), and $X_5$ or $X_7$ (but not both) represents an arginine or lysine having the same chirality as $Arg_1$, $Arg_9$ and $Lys_3$. The remaining amino acids, i.e., the freely selectable positions, $X_2$, $X_4$, $X_6$, $X_8$ and $X_7$ (where $X_5$ is defined as the L-or D-lysine or arginine according to the above rules) or $X_5$ (where $X_7$ is defined as the L- or D-lysine or arginine according to the above rules), may be any L- or D-amino acid other than L-lysine, D-lysine, L-arginine or D-arginine. The term freely selectable positions or residues also references those amino acid residues (where present) in the corresponding positions in the residue-spacer constructs of the invention. As further defined herein, the invention also encompasses the replacement of the freely-selectable amino acids with chemical spacers to form residue-spacer constructs such that the relative 3D orientation of the 2 arginines, 1 lysine, and 1 arginine or lysine is equivalent to that of $Arg_1$, $Lys_3$, Arg/$Lys_{(5\ or\ 7)}$ and $Arg_9$ of consensus sequences (i) and (ii). The chemical spacers/linkers that may replace the freely selectable amino acid in the molecules of the invention (e.g., a residue-spacer construct) are represented by ($SP_A$), ($SP_B$), and ($SP_C$) in consensus structures (iii) to (vi), and (xi) to (xiv); and by ($CL_A$), ($CL_B$) and ($CL_C$) in consensus structures (vii) to (x).

In the context of the present invention, L-amino acids, also known in the art and referenced herein as L-enantiomeric amino acids, are preferably amino acids selected from natively occurring amino acids or their derivatives. Naturally occurring amino acids are recognized as the standard (proteinogenic) amino acids alanine, arginine, asparagine, aspartic acid, cysteine, glutamine, glutaminic acid, glycine, histidine, isoleucine, leucine, lysine, methionine, phenyl alanine, proline, serine, threonine, tryptophan, tyrosine, and valine, but also include non-standard amino acids such as ornithine, citrulline, homocysteine, S-adenosyl methionione, hydroxyproline, selenocysteine, pyrrolysine, lanthionine, 2-aminoisobutyric acid, dehydroalanine, and gamma-aminobutyric acid.

Similarly, in the context of the present invention, D-amino acids, also known in the art and referenced herein as D-enantiomeric amino acids, are preferably non-native (non-proteinogenic) "retro-inverso" amino acids, wherein these non-native (non-proteinogenic) "retro-inverso" amino acids are recognized as derived from naturally occurring L-amino acids and/or their derivatives as defined above. In this context, the term "retro-inverso" refers to an isomer of a naturally occurring L-amino acid as defined above (and peptides made therefrom) in which the chirality of the naturally occurring L-amino acid residue is inverted in the corresponding D-amino acid. In other words, in the peptide bonds of D-amino acids the positions of carbonyl and amino groups are exchanged, while the position of the side-chain groups at each alpha carbon is preserved. Accordingly, D-amino acids may be inserted into a peptide sequence consisting of or comprising L-amino acids and therefore may be conjugated with L-amino acids as defined above by methods known in the art or defined herein.

Subject to the remaining selection rules as defined herein, where the consensus structures of the invention consist of or comprise exclusively amino acid residues, it is preferred, but not required, that the molecules and compounds of the invention corresponding to these consensus structures comprise at least one L-amino acid residue and at least one D-amino acid residue.

The amino acids abbreviations used in the present disclosure are shown in the following Table of Correspondence.

As used throughout the present disclosure and as detailed in the following table, upper-case or a capital letter in the 1 letter symbol references an L-amino acid, while a lowercase 1 letter symbol references a D-amino acid.

| Symbol | | | |
|---|---|---|---|
| 1-Letter | | | |
| L-amino acid | D-amino acid | 3-Letter | Amino acid |
| A | a | Ala | Alanine |
| R | r | Arg | Arginine |
| N | n | Asn | Asparagine |
| D | d | Asp | Aspartic acid |
| C | c | Cys | Cysteine |
| E | e | Glu | Glutamic acid |
| Q | q | Gln | Glutamine |
| G | g | Gly | Glycine |
| H | h | His | Histidine |
| I | i | Ile | Isoleucine |
| L | l | Leu | Leucine |
| K | k | Lys | Lysine |
| M | m | Met | Methionine |
| F | f | Phe | Phenylalanine |
| P | p | Pro | Proline |
| S | s | Ser | Serine |
| T | t | Thr | Threonine |
| W | w | Trp | Tryptophan |
| Y | y | Tyr | Tyrosine |
| V | v | Val | Valine |
| X | x | Xaa | Unknown or other |

As used herein, the term "peptides", "polypeptides" and "proteins" have their meaning as generally understood as in the art, i.e., referring to a chain of amino acids. However, the terms shall not be construed as limiting the length of the amino acid chain.

5. BRIEF DESCRIPTION OF FIGURES

FIG. 1 Schematic detailing the average distances between potentially interacting chemical residues of TAT and C6S. The boxed numbers identify the residue numbering for each molecule used in the simulations and as described herein. The figure details, in particular, the alternative interaction with the residues at positions 1, 3, 5 and 9 of the C6S binding molecule.

Figure 2:
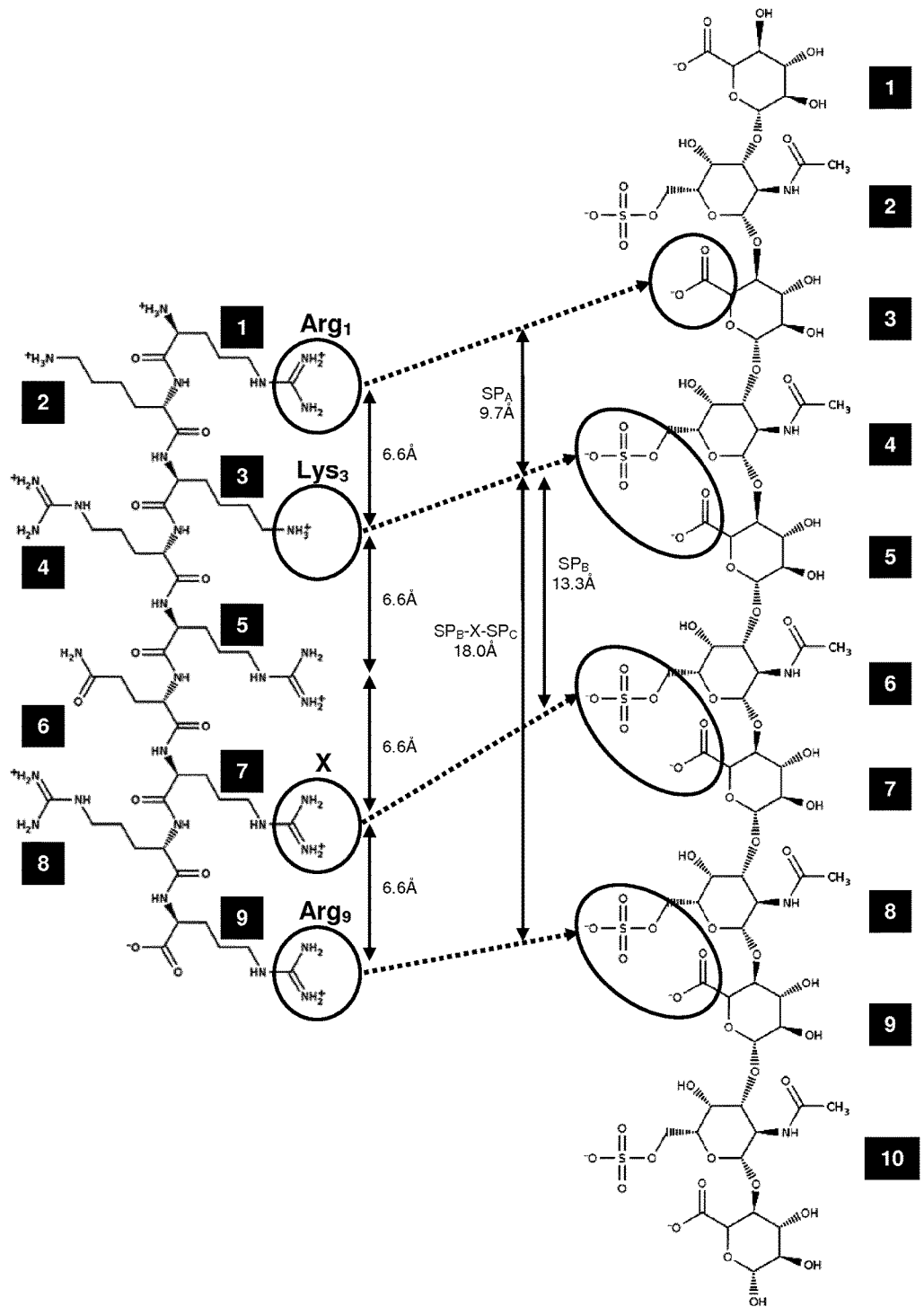

FIG. 2 Schematic detailing the average distances between potentially interacting chemical residues of TAT and C6S. The boxed numbers identify the residue numbering for each molecule used in the simulations and as described herein. The figure details, in particular, the alternative interaction with the residues at positions 1, 3, 7 and 9 of the C6S binding molecule.

Figure 3:
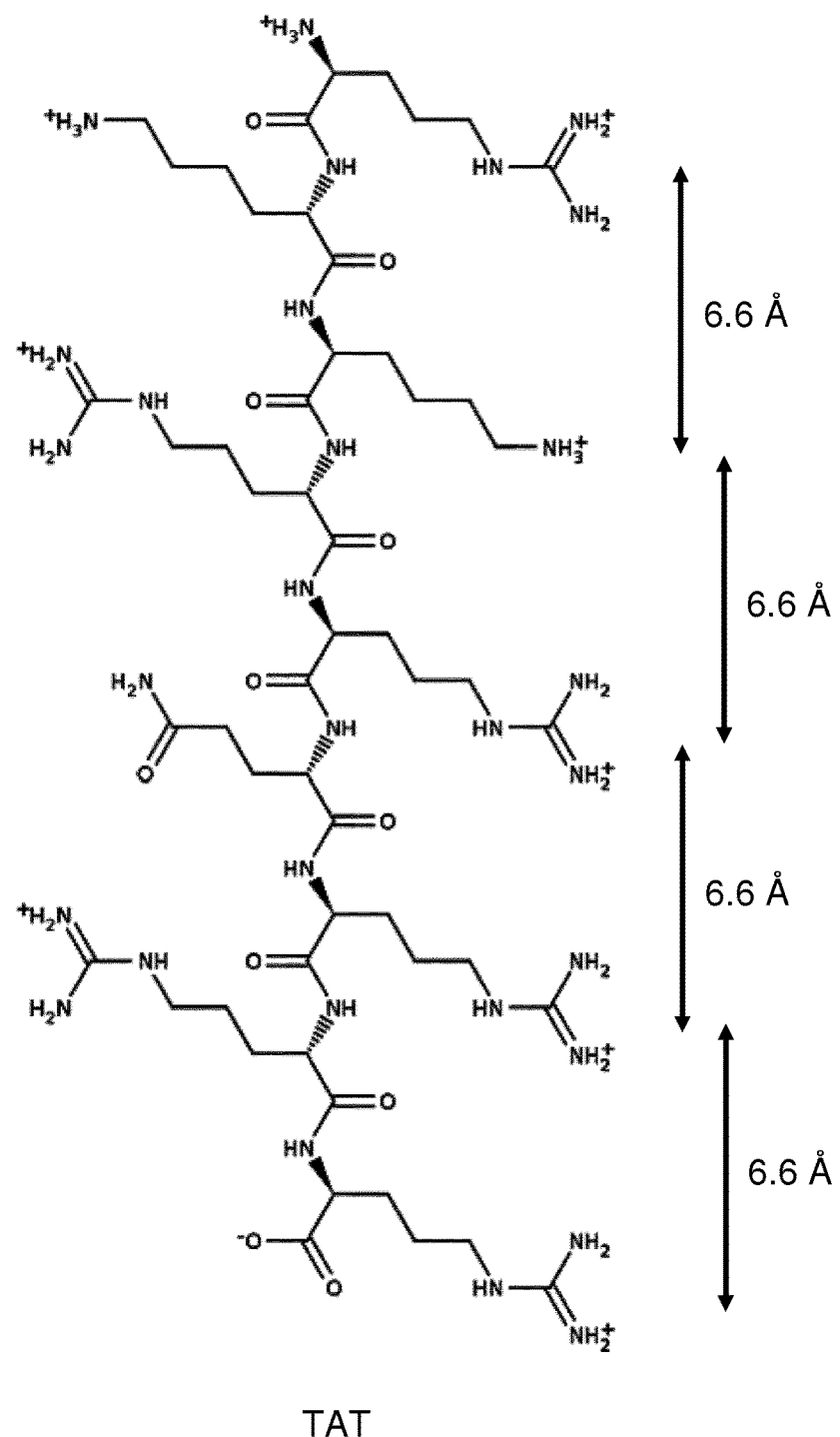

FIG. 3 Representation of TAT peptide in extended conformation, indicating calculated distances between certain chemical groups according to model predictions.

Figure 4:
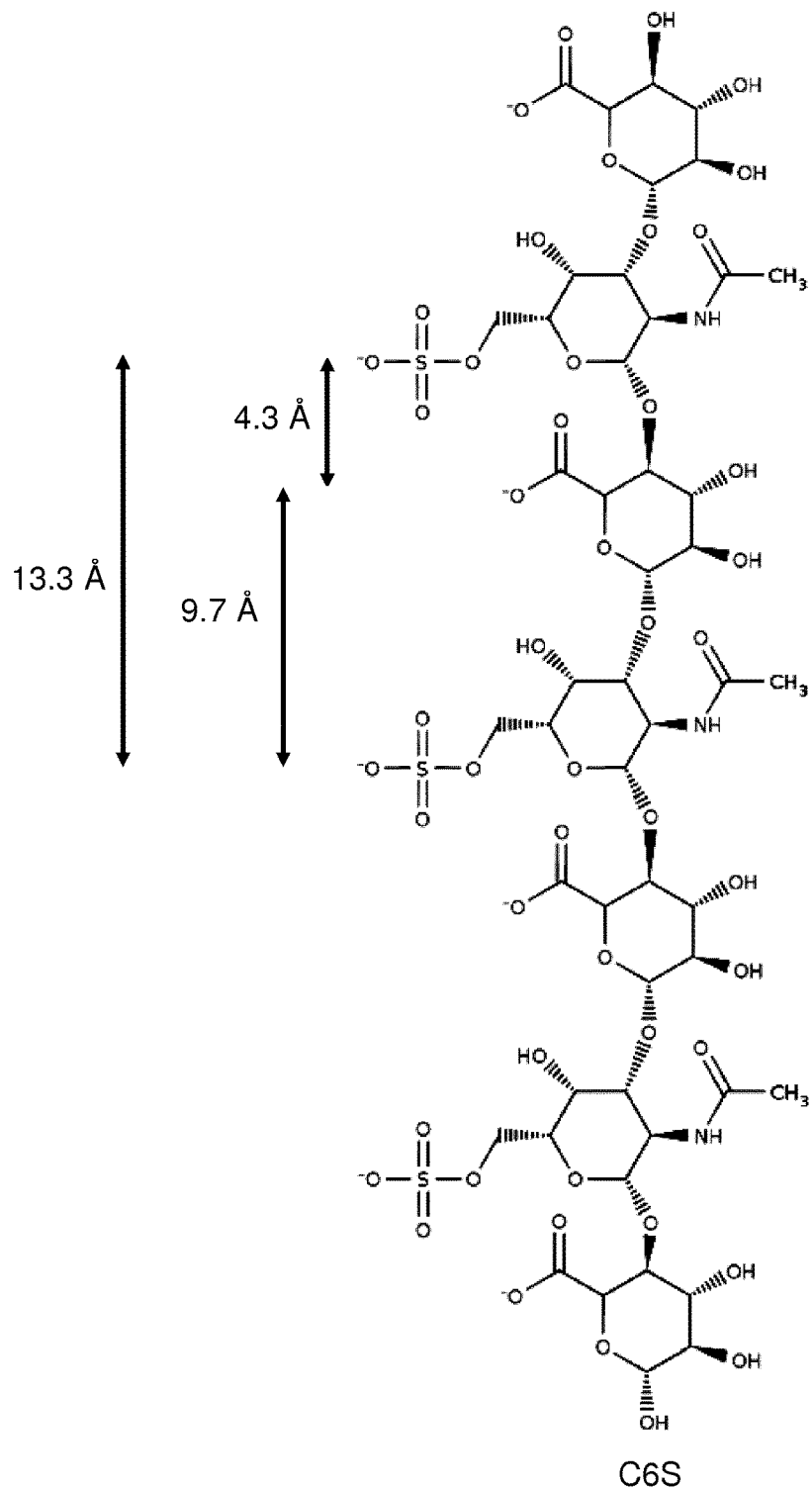

FIG. 4 Representation of C6S molecule in extended conformation, indicating calculated distances between certain chemical groups according to model predictions.

FIG. 5 Binding of a peptide of the invention having the sequence RYKvFIKYRh ("RYK-C65" SEQ ID NO:8) to various proteoglycans (5A) as compared to the binding of the TAT peptide (5B); HS: heparan sulfate; C4S: chondroitin-4-sulfate; C6S: chondroitin-6-sulfate; KS: keratin sulfate. The RYK-C6S peptide of the invention specifically and selectively binds C6S over other proteoglycans.

FIG. 6 (6A) Binding of peptides according to the invention and controls to C6S. Upper case letters indicate L-enantiomers and lower case letters indicate D-enantiomers. The tested peptides are RKKRRQRR (SEQ ID NO:25), RRRRRRRRR (SEQ ID NO:26), RYKvFIKYRh (SEQ ID NO:8), RYKvAIKYRh (SEQ ID NO:10), RYKvRIAYRh (SEQ ID NO:12), RYKvRIFYRh (SEQ ID NO:14), RYKvKFIYRh (SEQ ID NO:16), RYKvFIRYRh (SEQ ID NO:18), RYKvRFIYRh (SEQ ID NO:20), RMKiVMKFRh (SEQ ID NO:22), RFKfFFKFRh (SEQ ID NO:24), RYKvFIKPRh (SEQ ID NO:27) and RYFvRIKYR (SEQ ID NO:28). (6B) Binding of peptides according to the invention and controls to C4S, C6S, KS, HS and HA. The tested peptides are RYKvFIKYRh (SEQ ID NO:8), comprising RGKPRFYQR (SEQ ID NO:31), comprising RGKpRFYQR (SEQ ID NO:32) and RFKGSWKYR (SEQ ID NO:33). Binding to C6S is maintained where consensus sequences (i) and/or (ii) are followed. Binding is maintained where the freely selectable positions are mutated to comprise various residues except proline.

Figure 7:
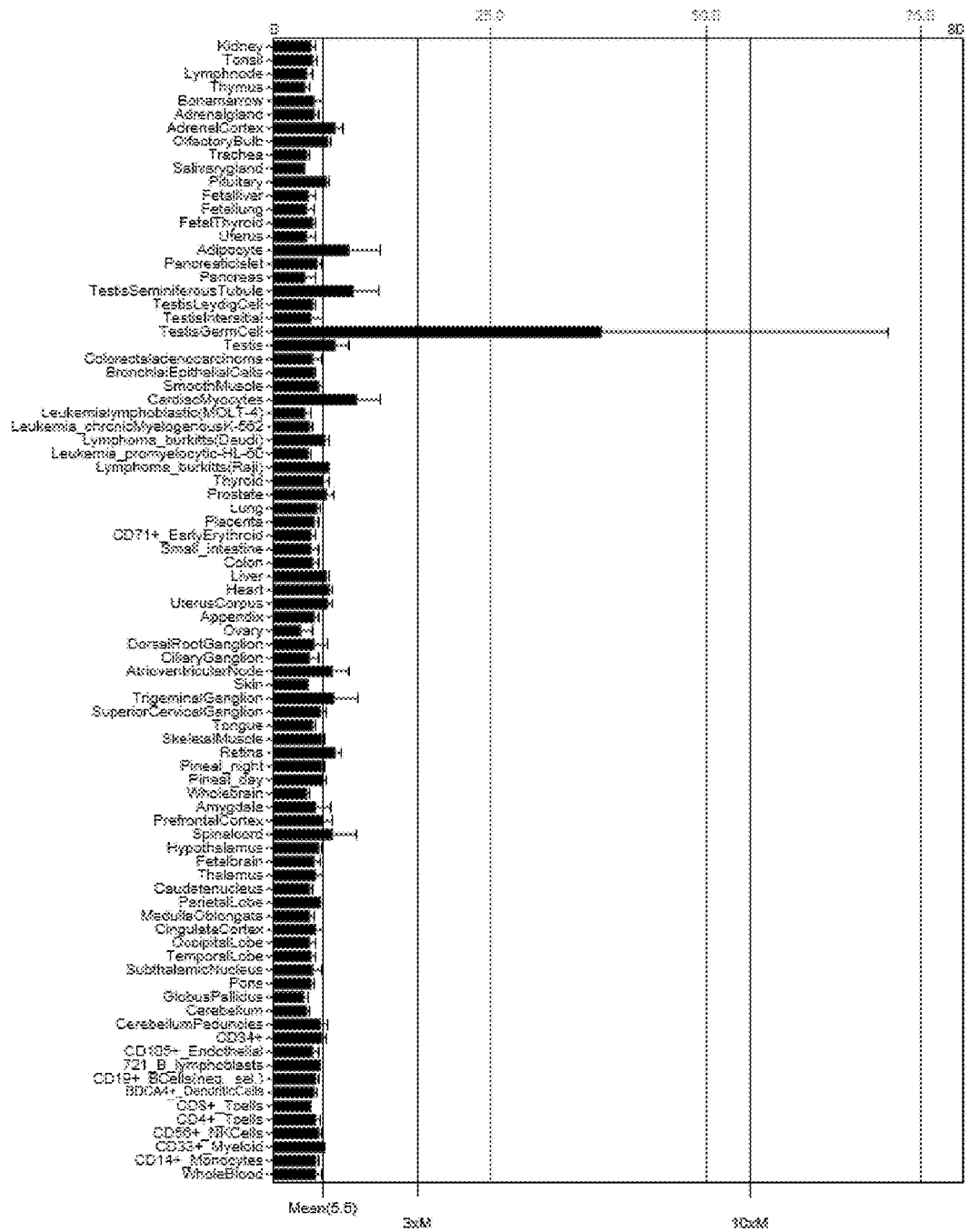

FIG. 7 CHST3 expression data from Atlas arrays.

Figure 8:
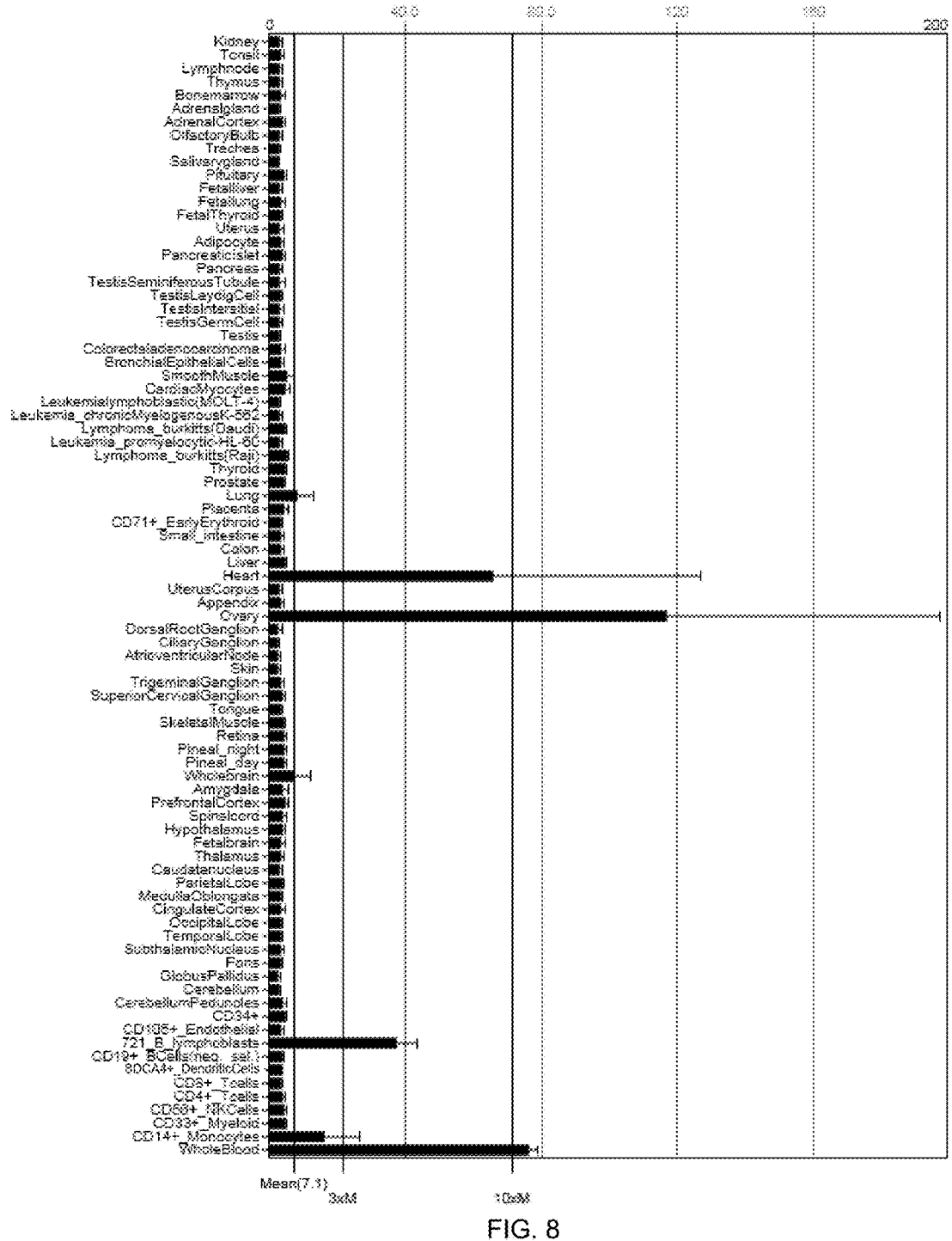

FIG. 8 CHST7 expression data from Atlas arrays.

Figure 9:
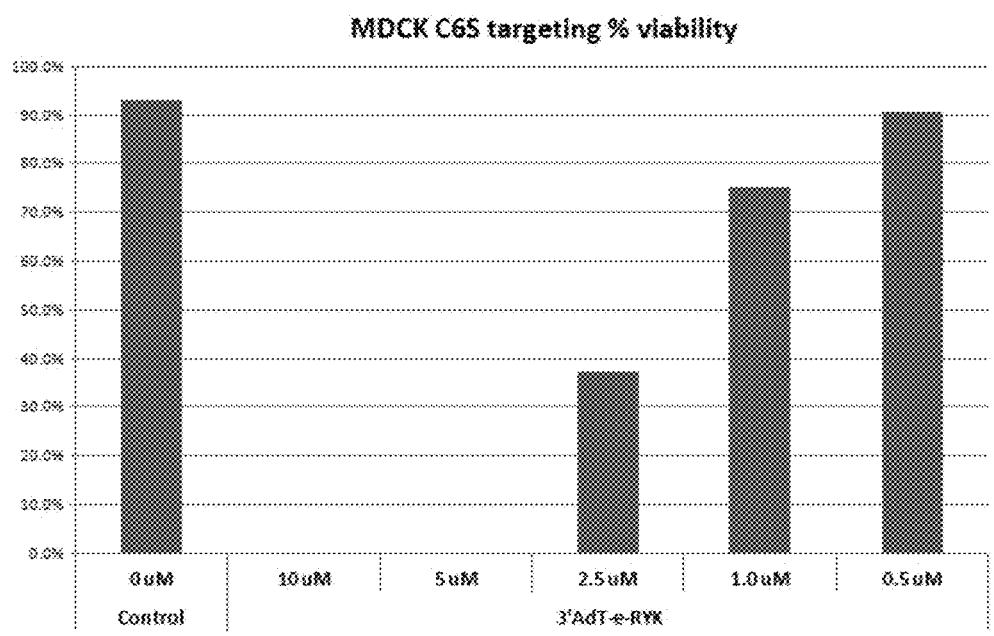

FIG. 9 Percent viability of MDCK cell cultures following exposure to a model BAM-conjugate. Viability was determined by trypan blue exclusion following 96 hour incubation with different concentrations of 3'AdT conjugated to the amino-terminus of the peptide "RYK" (RYKvFIKYRh (SEQ ID NO:8)) using a single D-Glu residue (3'AdT-e-RYK).

6. DETAILED DESCRIPTION OF THE INVENTION

The present invention relates to molecules, peptides, polypeptides and compounds comprising or consisting of such molecules, peptides or polypeptides having specific consensus sequences or structures and their use for specific transport of biologically active moieties (BAMs) to the intercellular environment, i.e., the cytoplasm and/or the nucleus. The inventors have surprisingly discovered that certain consensus structures or sequences of molecules and peptides are able to selectively target specific proteoglycans, in particular chondroitin 6-sulfate (C6S). Accordingly, the molecules, proteins, polypeptides and compounds comprising or consisting of such molecules, peptide or polypeptide comprising or consisting of one or more of the consensus sequences disclosed herein may find particular use as transport moieties for the targeted delivery of BAMs to cells expressing C6S.

Although the binding of certain peptides to proteoglycans and phospholipids is known, it has previously been viewed as a non-specific process driven primarily though ubiquitous hydrostatic interactions. As such, it has not been previously suggested that such interactions can be manipulated to impart selectivity, preventing the peptides from being used for specific targeting. Despite the perceived ubiquitous nature of these interactions, the present inventors have surprisingly discovered that specific peptide sequences can be designed that exhibit selectivity for certain proteoglycans over phospholipids in general. Specifically, the present inventors have discovered that a peptide comprising a 9 residue sequence having arginines at positions 1 and 9, a lysine at position 3, and an arginine or a lysine at position 5 or 7 (but not both), or a molecular construct exhibiting an equivalent relative 3D confirmation of these 4 residues (e.g., a residue-spacer construct), optimally interacts via electrostatic bridging with the sulfates and carboxylates on the aminoglycan units of C6S. Moreover, including non-charged amino acids or non-positively charged chemical spacers in the remaining positions provides selectivity, inhibiting or substantially reducing the non-specific interaction of the peptide with other proteoglycans and/or phospholipids. Thus, the unique combination of residues and/or 3D presentation of specific residues allow peptides and residue-spacer constructs to be designed that exhibit selective binding for C6S proteoglycans over other proteoglycans and other phospholipids.

The remaining residues within the 9-mer, i.e., the freely selectable residues at positions 2, 4, 6, 8 and 7 (where the residue at position 5 is defined as the L- or D-lysine or arginine according to the above rules) or 5 (where the residue at position 7 is defined as the L- or D-lysine or arginine according to the above rules), are not predicted by the model to be involved in the binding of the peptide to C6S, and, provided the three dimensional linear conformation of residues at positions 1, 3, (5 or 7), and 9 is not disturbed in the peptide, substitution with a wide variety of amino acids (including non-natural amino acids, such as D-amino acids) at these freely selectable positions had little to no effect on the specific binding to C6S. Accordingly, the inventors surprisingly discovered that provided the 3D presentation and/or orientation of these 2 arginine residues, 1 lysine residue, and 1 arginine or lysine residue is maintained in the molecule, C6S specific binding will also be maintained. Therefore, the invention encompasses the replacement of the residues at these freely-selectable positions with chemical spacers or combinations of amino acids and chemical spacers provided that the relative 3D orientation of the arginines at positions 1 and 9, the lysine at position 3, and the arginine or lysine at position 5 or 7 (but not both) is maintained so as to be equivalent to their presentation in consensus sequences (i) and/or (ii) (in particular with respect to their side chains). However, the use of the charged amino acids arginine or lysine in these freely selectable positions (where amino acid residues are present) and/or charged linking groups, in particular positively charged groups, increased the likelihood of non-specific interactions with other proteoglycans and phospholipids. Therefore, to maintain specificity, the use of arginine and lysine in the freely selectable positions is avoided in the peptides of the invention and/or the use of charged linking groups is avoided where one or more of the freely selectable residues are replaced by a chemical linker in the residue-linker constructs of the invention.

Additionally, it was discovered that specificity can be maintained using D-amino acids in the molecules of the invention (e.g., peptides or residue-spacer constructs) at the positions relevant for C6S binding, i.e., Arg1, Lys3, Arg/Lys(5 or 7), and Arg9, provided that all positions have the same chirality. It is believed that the use of a single chirality at these positions presents the same three-dimensional structure of the amino acid side chains. Where one or more of these positions has a differing chirality, the three-dimensional liner arrangement is distorted. Thus, the invention encompasses a molecule comprising 2 arginine residues, 1 lysine residue and 1 arginine or lysine residue, wherein each of the 4 residues is a L-residue or wherein each of the 4 residues is a D-residue, provided that the molecule presents the residues in the same or similar 3D orientation and configuration as Arg1, Lys3, Arg/Lys(5 or 7), and Arg9 in consensus sequences (i) and (ii) (in particular, when the molecules are in solution).

Additionally, where the molecules and compounds are designed/selected such that this single Arg/Lys residue is to correspond to position 7 of consensus sequences (i) or (ii) (and, thus, not position 5 thereof, i.e., to correspond to X of consensus sequences (iii), (v), (vii) and/or (ix)), it is preferred, but not required that the residue is an L-lysine residue (where Arg1, Lys3 and Arg9 are L-amino acids) or a D-lysine residue (where Arg1, Lys3 and Arg9 are D-amino acids).

The consensus sequences of the molecules of the invention are preferably envisioned as transporter moieties, of use in the intercellular transport of associated cargo molecules/moieties. Proteoglycans and/or molecules comprising proteoglycans on the cellular surface are known to be cycled via endosomes. To favor release of the compound of the invention from the endosome (and help further avoid degradation), one to several amino acid residues capable of acting as a proton sponge can optionally be added to the N- or C-terminus of the transporter moiety. The proton sponge increases the osmolarity of the endosome, causing swelling and rupture, leading to cytosolic release of its contents rather than their degradation. Any amino acid residue or combination of residues known in the art or described herein capable of functioning as a proton sponge can be used in accordance with the invention. The final amino acid of this optional series of proton sponge residues (i.e., the final N-terminal or C-terminal residue of the proton sponge residues (where present)) may also optionally be a D-entantiomer to avoid degradation/cleavage of the proton sponge residues. Accordingly, the invention encompasses the optional use of one or more amino acid residues added to the N- or C-terminus of the transporter moiety, wherein the N- or C-terminal residue, respectively, is optionally a D-entantiomer. In preferred embodiments, the one or more residues of the proton sponge residues is(are) not lysine or arginine residues. The optional residues of the proton sponge as defined herein are represented in the consensus sequences (i) to (xiv) of the invention by $LD_{10}$ or $LD_{-1}$. The optional N- or C-terminal residue of the proton sponge is represented in the consensus sequences (i) to (xiv) of the invention by $XD_{11}$ or $XD_{-2}$. Thus, in preferred embodiments, $LD_{10}$ or $LD_{-1}$ of consensus sequences (i) to (xiv) (where present) represents any L- or D-amino acid other than L- or D-arginine or L- or D-lysine; in connection with these preferred embodiments or as independent embodiments, $XD_{11}$ or $XD_{-2}$ of consensus sequences (i) to (xiv) (where present) is preferentially any D-amino acid other than D-arginine or D-lysine. In more preferred embodiments, the one or more residues of the proton sponge residues is(are) histidine residues. In the most preferred embodiments, $LD_{10}$ or $LD_{-1}$ of consensus sequences (i) to (xiv) represents L- or D-histidine; in connection with these most preferred embodiments or as independent embodiments, $XD_{11}$ or $XD_{-2}$ of consensus sequences (i) to (xiv) is most preferentially D-histidine.

6.1 Molecule Consensus Structures

The above discoveries of the inventors may be presented as a consensus structure. The invention is generally directed to at least one isolated molecule, or compounds comprising or consisting of said molecule, wherein the molecule has a consensus structure according to (iii) to (vi), or the reverses thereof:

(iii)
$Arg_1$-$(SP_A)$-$Lys_3$-$(SP_B)$-X-$(SP_C)$-$Arg_9$-$(LD_{10})_n$-$(XD_{11})_m$;

(iv)
$Arg_1$-$(SP_A)$-$Lys_3$-$(SP_C)$-X-$(SP_B)$-$Arg_9$-$(LD_{10})_n$-$(XD_{11})_m$;

-continued (v)
$(XD_{-2})_m-(LD_{-1})_n-Arg_1-(SP_A)-Lys_3-(SP_B)-X-(SP_C)-Arg_9;$
or (vi)
$(XD_{-2})_m-(LD_{-1})_n-Arg_1-(SP_A)-Lys_3-(SP_C)-X-(SP_B)-Arg_9;$ wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein (a) $Arg_1$ and $Arg_9$ represent L-arginine, $Lys_3$ represents L-lysine, and X represents L-arginine or L-lysine;

or (b) $Arg_1$ and $Arg_9$ represent D-arginine, $Lys_3$ represents D-lysine, and X represents D-arginine or D-lysine;

wherein ($SP_A$) represents a chemical linker that (a) consists of a single amino acid residue, which may be any L- or D-amino acid residue other than D-arginine, D-lysine, L-arginine or L-lysine;

or (b) separates the adjacent amino acid residues by 9.7±1.5 Å when the molecule is in extended conformation;

wherein ($SP_B$) represents a chemical linker that (a) consists of a peptide chain of 3 amino acid residues, each of which may be independently selected from any L- or D-amino acid residue other than D-arginine, D-lysine, L-arginine or L-lysine;

or (b) separates the adjacent amino acid residues by 13.3±1.5 Å when the molecule is in extended conformation;

and wherein ($SP_C$) represents a chemical linker that (a) consists of a single amino acid residue, which may be any L- or D-amino acid residue other than D-arginine, D-lysine, L-arginine or L-lysine;

or (b) contributes to the linker $(SP_B)-X-(SP_C)$ such that it or its reverse, $(SP_C)-X-(SP_B)$ separates $Lys_3$ and $Arg_9$ by 18.0±1.5 Å when the molecule is in extended conformation.

When the molecule or compound of the invention comprises one or more chemical spacers/linkers that is not an amino acid residue or is not comprised exclusively of amino acids, care must be taken such that the side chains of Arg1, Lys3, Arg/Lys(5 or 7) and Arg9 retain the same or similar 3D presentation as their counterpart side chains in the peptide and/or polypeptide consensus sequences (i) and/or (ii) as defined herein. Thus, the side chains of Arg1, Lys3, Arg/Lys(5 or 7) and Arg9 within residue-spacer constructs according to the methods of the invention should present in a linear or near linear arrangement within 3D space when the molecule and/or construct is in extended conformation.

6.2 Peptide Consensus Sequences

In embodiments of the invention wherein the molecules and/or compounds according to consensus structures (iii) to (vi) comprise or consist only of amino acid residues, the consensus structures may be represented by consensus sequences of a peptide or polypeptide. Accordingly, in certain embodiments, the present invention is directed to compounds comprising or consisting of at least one isolated peptide or polypeptide having an amino acid sequence according to the following consensus sequence (i) or (ii), or the reverses thereof:

(i)
$Arg_1-X_2-Lys_3-X_4-X_5-X_6-X_7-X_8-Arg_9-(LD_{10})_n-(XD_{11})_m,$
or (ii)
$(XD_{-2})_m-(LD_{-1})_n-Arg_1-X_2-Lys_3-X_4-X_5-X_6-X_7-X_8-Arg_9$ wherein, (a) $Arg_1$ and $Arg_9$ represent L-arginine; $Lys_3$ represents L-lysine; $LD_{10}$ or $LD_{-1}$ represents any L- or D-amino acid other than D-arginine, D-lysine; L-arginine or L-lysine and n has a value of 0 to 10; $XD_{11}$ or $XD_{-2}$ represents any D-amino acid other than D-arginine or D-lysine and m has a value of 0 or 1; and wherein the remaining amino acids $X_4$ to $X_5$ may be independently selected from any L- or D-amino acid other than D-arginine, D-lysine, L-arginine or L-lysine, with the proviso that either $X_5$ or $X_7$, but not both, represents L-lysine or L-arginine;

or wherein, (b) $Arg_1$ and $Arg_9$ represent D-arginine; $Lys_3$ represents D-lysine; $LD_{10}$ or $LD_{-1}$ represents any L- or D-amino acid other than D-arginine, D-lysine; L-arginine or L-lysine and n has a value of 0 to 10; $XD_{11}$ or $XD_{-2}$ represents any D-amino acid other than D-arginine or D-lysine and m has a value of 0 or 1; and wherein the remaining amino acids $X_4$ to $X_8$ may be independently selected from any L- or D-amino acid other than D-arginine, D-lysine, L-arginine or L-lysine, with the proviso that either $X_5$ or $X_7$, but not both, represents D-lysine or L-arginine.

Consensus sequence (i), above, with conditions (a) is SEQ ID NO:1, and with conditions (b) is SEQ ID NO:2. Consensus sequence (ii), above, with conditions (a) is SEQ ID NO:3, and with conditions (b) is SEQ ID NO:4.

6.3 Residue-Spacer Consensus Structures

In embodiments of the invention wherein the chemical linkers/spacers represented by $SP_A$, $SP_B$, and $SP_C$ in consensus structures (iii) to (vi) do not comprise amino acid residues, the consensus structures may be represented by consensus structures for a residue-spacer construct. In such embodiments, the invention can be defined as directed to at least one residue-spacer construct, or compounds comprising or consisting of them, wherein the construct has a consensus structure according to (vii) to (x), or the reverses thereof:

(vii)
$Arg_1-(CL_A)-Lys_3-(CL_B)-X-(CL_C)-Arg_9-(LD_{10})_n-(XD_{11})_m;$ (viii)
$Arg_1-(CL_A)-Lys_3-(CL_C)-X-(CL_B)-Arg_9-(LD_{10})_n-(XD_{11})_m;$ (ix)
$(XD_{-2})_m-(LD_{-1})_n-Arg_1-(CL_A)-Lys_3-(CL_B)-X-(CL_C)-Arg_9;$
or (x)
$(XD_{-2})_m-(LD_{-1})_n-Arg_1-(CL_A)-Lys_3-(CL_C)-X-(CL_B)-Arg_9;$ wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein (a) $Arg_1$ and $Arg_9$ represent L-arginine, $Lys_3$ represents L-lysine, and X represents L-arginine or L-lysine;

or (b) $Arg_1$ and $Arg_9$ represent D-arginine, $Lys_3$ represents D-lysine, and X represents D-arginine or D-lysine;

wherein ($CL_A$) represents a chemical linker that separates the adjacent amino acid residues by 9.7±1.5 Å when the molecule is in extended conformation;

wherein ($CL_B$) represents a chemical linker that separates the adjacent amino acid residues by 13.3±1.5 Å when the molecule is in extended conformation;

and wherein ($CL_C$) represents a chemical linker that contributes to the linker ($CL_B$)-X-($CL_C$) such that it or its reverse, ($CL_C$)-X-($CL_B$), separates $Lys_3$ and $Arg_9$ by 18.0±1.5 Å when the molecule is in extended conformation.

When the molecule or compound of the invention comprises one or more chemical spacers/linkers that is not exclusively comprised of amino acid residues, care must be taken such that the side chains of Arg1, Lys3, Arg/Lys(5 or 7) and Arg9 retain the same or similar 3D presentation as their counterpart side chains in the peptide and/or polypeptide consensus sequences (i) and/or (ii). Thus, the side chains of Arg1, Lys3, Arg/Lys(5 or 7) and Arg9 within residue-spacer constructs according to the methods of the invention should present in a linear or near linear arrangement within 3D space when the molecule and/or construct is in extended conformation.

6.4 Targeting Moieties

The molecules and compounds described above according to consensus sequences (iii) to (vi) find particular use as transport and/or targeting moieties, specifically recognizing and/or binding proteoglycans, e.g., as expressed on the surface of a cell, in particular, binding the proteoglycan C6S selectively over other proteoglycans. The portion of the above consensus sequences (iii) to (vi) acting as the targeting moiety that specifically interact with the C6S proteoglycan is represented by

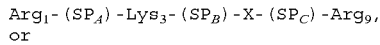

$Arg_1$-($SP_A$)-$Lys_3$-($SP_B$)-X-($SP_C$)-$Arg_9$, or $Arg_1$-($SP_A$)-$Lys_3$-($SP_C$)-X-($SP_B$)-$Arg_9$

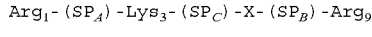

These targeting moieties include the specific embodiments having consensus sequences or structures comprised exclusively of amino acids, i.e., $Arg_1$-$X_2$-$Lys_3$-$X_4$-$X_5$-$X_6$-$X_7$-$X_8$-$Arg_9$, wherein $X_5$ or $X_7$ is an arginine or a lysine residue (SEQ ID NO:5, where a fragment of SEQ ID NO:1 or SEQ ID NO:3; SEQ ID NO:6, where a fragment of SEQ ID NO:2 or SEQ ID NO:4)). These moieties also include specific embodiments wherein the freely selectable positions are replaced by chemical linkers and/or the combination of chemical linkers and amino acids, i.e., $Arg_1$-($CL_A$)-$Lys_3$-($CL_B$)-X-($CL_C$)-$Lys_9$ or $Arg_1$-($CL_A$)-$Lys_3$-($CL_C$)-X-($CL_B$)-$Lys_9$. The targeting moieties are identical molecules with respect to the 3D presentation of the amino acid residues corresponding to Arg1, Lys3, Arg/Lys(5 or 7) and Arg9 in consensus sequences (i) and (ii), and, in particular, the sides chains of these residues. Accordingly, any molecule comprising 2 arginine residues, 1 lysine residue and 1 arginine or lysine residue according to consensus sequences (iii) to (vi) can be developed as the targeting moiety according to the following rules:

(1) Each of the residues Arg1, Lys3, and Arg9 must have the same chirality, i.e., each must be an L-amino acid or each must be a D-amino acid.

(2) Arg1 must be linked to Lys3 using a chemical spacer, which spacer may be either (a) any L- or D-amino acid other than D-arginine, D-lysine; L-arginine or L-lysine; or (b) a chemical spacer that separates the amino acids by 9.7±1.5 Å when the molecule is in an extended conformation.

(3) Lys3 must be linked to Arg9 using one or more chemical spacers, which spacer may either
   (a) consist exclusively of a peptide chain of 5 amino acid residues having a single arginine or lysine residue that has the same chirality as Arg1, Lys3 and Arg9, and having the remaining 4 residues independently selected from any L- or D-amino acid other than D-arginine, D-lysine; L-arginine or L-lysine; or
   (b) comprise at least one amino acid residue and one or more chemical linkers such that Lys3 and Arg9 are separated by 18.0±1.5 Å when the molecule is in an extended conformation, wherein, if more than one amino acid residue is present, only one amino acid residue is an arginine or lysine having the same chirality as Arg1, Lys3 and Arg9, and any remaining residue(s) is(are) independently selected from any L- or D-amino acid other than D-arginine, D-lysine; L-arginine or L-lysine.

(4) The single arginine or lysine residue in the spacer defined according to rule (3)(a) or (b) (i.e., linking Lys3 and Arg9) corresponds to $X_5$ or $X_7$ in consensus sequences (i) or (ii) and/or to X in consensus sequences (iii) to (vi). This Arg/Lys residue (i.e., Arg/Lys(5 or 7) as defined herein) is positioned within the spacer construct according to rule (3) above such that (a) it is separated from either Lys3 or Arg9 by a peptide chain consisting of 3 amino acid residues that are independently selected from any L- or D-amino acids other than D-arginine, D-lysine; L-arginine or L-lysine; or (b) it is separated from either Lys3 or Arg9 by 13.3±1.5 Å when the molecule is in an extended conformation.

(5) Where one or more of the linkages between Arg1 and Lys3, between Lys3 and Arg/Lys(5 or 7), and between Arg/Lys(5 or 7) and Arg9 are not exclusively amino acid residues, i.e., are chemical spacers/linkers or residue-spacer constructs (i.e., comprising both amino acids and chemical linkers), they may comprise any chemical spacer or linker known in the art and/or described herein suitable for maintaining the required separation between Arg1 and Lys3, between Lys3 and Arg/Lys(5 or 7), or between Arg/Lys(5 or 7) and Arg9 as well as suitable to maintain a 3D orientation and/or 3/D presentation of these amino acids (in particular, their side chains) similar to or the same as that in the corresponding residues in consensus sequences (i) and (ii). The linkages between Arg1 and Lys3, between Lys3 and Arg/Lys(5 or 7), and between Arg/Lys(5 or 7) and Arg9 should preferentially not be positively charged.

6.5 Chemical Linkers $SP_A$, $SP_B$, and $SP_C$ in consensus sequences (iii) to (vi) represent chemical linkers/spacers that form part of the backbone of the molecule of the invention and each may comprise or consist of exclusively of one or more amino acid residues, may comprise or consist of one or more chemical linkers (i.e., that are not amino acid residues), or may comprise or consist of both amino acid residues and chemical linkers. Chemical linkers that are not amino acid residues that are of use according to the methods of the invention may be any appropriate chemical linker or chemical spacer suitable to maintain the spacing and the relative 3D orientation/presentation of the 2 arginine residues (i.e., $Arg_1$ and $Arg_9$), the 1 lysine residues (i.e., $Lys_3$), and the 1 arginine or lysine residue (i.e., Arg/Lys(5 or 7)) equivalent to the corresponding residues in consensus sequences (i) and (ii). Any such chemical linker/spacer known in the art or described herein may be used in the construction of the molecules of the invention, and it is within the abilities of one of skill in the art to select and adapt such linkers to the methods of the invention. Nonlimiting examples of appropriate chemical linkers/spacers include beta- and gamma-peptides such as those disclosed and described in e.g. Seebach et al., *Chem. Biodivers.* 1(2004), 1111-1239; sugar amino acid based scaffolds such as those disclosed and described in e.g., Chakraborty et al., *Comb. Chem. High Throughput Screen.* 5(2002), 373-387; beta-hairpin peptidomimetics such as those disclosed and described in e.g., Robinson, *Acc. Chem. Res.* 41(2008), 1278-1288; alpha-helical mimetics, beta-sheet/beta-stand mimetics and beta-turn mimetics such as those disclosed and described in e.g., Hershberger et al., *Curr. Top. Med. Chem.* 7(2007), 928-924 and cyclotides such as those disclosed and described in e.g., Jagadish and Camarero, *Biopolymers* 94(2010), 611-616. In preferred embodiments, the chemical linker/spacers are not positively charged.

6.6 BAM Conjugates

As detailed herein, the molecules and compounds of the invention comprising or consisting of the molecules, peptides and/or polypeptides according to consensus sequences and structures (i) to (x) are envisioned in preferred embodiments to function as transporter moieties capable of specifically transporting associated cargo molecules/moieties. In preferred embodiments, the molecules and compounds of the invention comprise or consist of the sequences and/or structures according to any of consensus sequences (i) to (x) further conjugated to a biologically active moiety (BAM); the structure is referenced as a BAM-conjugate throughout this description. The BAM is any moiety known or expected to exhibit a therapeutic effect when administered to an organism, or when introduced to a cell, either in vitro or in vivo. In preferred embodiments, the compounds of the invention comprise or consist of a BAM-conjugate, having a BAM conjugated at the terminus of a consensus sequence or structure (i) to (x) as described herein. Therefore, in these preferred embodiments, the BAM-conjugate has a consensus structure according to the following consensus structures (xi) to (xiv), or the reverses thereof:

(xi)
(BAM)-(LINK)-$Arg_1$-($SP_A$)-$Lys_3$-($SP_B$)-X-($SP_C$)-$Arg_9$-($LD_{10}$)$_n$-($XD_{11}$)$_m$;

(xii)
(BAM)-(LINK)-$Arg_1$-($SP_A$)-$Lys_3$-($SP_C$)-X-($SP_B$)-$Arg_9$-($LD_{10}$)$_n$-($XD_{11}$)$_m$;

(xiii)
($XD_{-2}$)$_m$-($LD_{-1}$)$_n$-$Arg_1$-($SP_A$)-$Lys_3$-($SP_B$)-X-($SP_C$)-$Arg_9$-(LINK)-(BAM);

(xiv)
($XD_{-2}$)$_m$-($LD_{-1}$)$_n$-$Arg_1$-($SP_A$)-$Lys_3$-($SP_C$)-X-($SP_B$)-$Arg_9$-(LINK)-(BAM);

wherein (BAM) represents a biologically active moiety; wherein (LINK) represents an optional linker group; wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;
wherein
(a) $Arg_1$ and $Arg_9$ represent L-arginine, $Lys_3$ represents L-lysine, and X represents L-arginine or L-lysine;
or
(b) $Arg_1$ and $Arg_9$ represent D-arginine, $Lys_3$ represents D-lysine, and X represents D-arginine or D-lysine;
wherein ($SP_A$) represents a chemical linker that
(a) consists of a single amino acid residue, which may be any L- or D-amino acid residue other than D-arginine, D-lysine, L-arginine or L-lysine;
or
(b) separates the adjacent amino acid residues by 9.7±1.5 Å when the molecule is in extended conformation;
wherein ($SP_B$) represents a chemical linker that
(a) consists of a peptide chain of 3 amino acid residues, which may be independently selected from any L- or D-amino acid residue other than D-arginine, D-lysine, L-arginine or L-lysine;
or
(b) separates the adjacent amino acid residues by 13.3±1.5 Å when the molecule is in extended conformation;
and wherein ($SP_C$) represents a chemical linker that
(a) consists of a single amino acid residue, which may be any L- or D-amino acid residue other than D-arginine, D-lysine, L-arginine or L-lysine;
or
(b) contributes to the linker ($SP_B$)-X-($SP_C$) such that it or its reverse, ($SP_C$)-X-($SP_B$), separates $Lys_3$ and $Arg_9$ by 18.0±1.5 Å when the molecule is in extended conformation.

6.6.1 The Optional Linking Group

Consensus sequences (xi) to (xiv) are identical to consensus sequences (iii) to (vi), respectively, but for the presence of the BAM-moiety and the optional linker group, (LINK). Therefore, selection of the chemical spacers ($SP_A$), ($SP_B$) and ($SP_C$), which, together, may consist of or comprise exclusively amino acid residues or comprise both chemical linkers and amino acid residues as described herein proceeds as described herein with respect to consensus sequences (iii) to (vi), including
selection of these chemical spacers to consist of or comprise exclusively amino acid residues according to the embodiments (and combinations thereof) of consensus sequences (i) and (ii) as detailed throughout this disclosure, and
selection of these chemical spacers to comprise chemical linkers or to comprise amino acid residues and chemical linkers according to the embodiments (and combinations thereof) of consensus structures (iii) to (x) as detailed throughout this disclosure.

The optional linking group (LINK) may be a peptidic linker. If peptidic linker sequences are used, the linker sequences preferably form a flexible sequence of 2 to 10 residues, more preferably 1 to 5 residues. In a preferred embodiment, the linker sequence contains at least 20%, more preferably at least 40% and even more preferably at least 50% Gly or β-alanine residues. Nonlimiting examples of linking groups include, GlyGlyGlyGlyGly (SEQ ID NO:29), GlyGlyGlyGly (SEQ ID NO:30), GlyGlyGly, Cys-GlyGly or GlyGlyCys, etc. Appropriate linker sequences are well known to and can be easily selected and prepared by a person skilled in the art. The optional linker group may be composed of D-amino acids, L amino acids, and/or combinations thereof.

Alternatively, the BAM and the transporter moiety may be linked by chemical coupling in any suitable manner known in the art or described herein, such as cross-linking methods. However, attention is drawn to the fact that many known chemical cross-linking methods are non-specific, i.e., they do not direct the point of coupling to any particular site on the carrier/transporter moiety or on the cargo moiety (e.g., BAM). Thus, the use of non-specific cross-linking agents may attack functional sites or sterically block active sites, rendering the one or both of the BAM/transporter components of the inventive BAM-conjugate molecule biologically inactive. It is referred to the knowledge of the skilled artisan to block potentially reactive groups by using appropriate protecting groups. Alternatively, the use of the powerful and versatile oxime and hydrazone ligation techniques, which are chemo-selective entities that can be applied for the cross-linking of component (A) to component (B), may be employed. This linking technology is described, e.g., by Rose et al. (1994), *JACS* 116, 30.

Coupling specificity can also be increased by direct chemical coupling to a functional group found only once or a few times in the BAM component and the transporter moiety. Coupling of the two components of the inventive peptide-conjugate molecule can be accomplished via a coupling or conjugating agent as is known in the art, including standard (poly-) peptide synthesis coupling reagents such as HOBt, HBTU, DICI, TBTU. There are several intermolecular cross-linking reagents which can be utilized, see, for example, Means and Feeney, *Chemical Modification of Proteins*, Holden-Day, 1974, pp. 39-43. These reagents include, but are not limited to, N-succinimidyl 3-(2-pyridyldithio)propionate (SPDP) or N,N'-(1,3-phenylene) bismaleimide; N,N'-ethylene-bis-(iodoacetamide) or other such reagent having 6 to 11 carbon methylene bridges; and 1,5-difluoro-2,4-dinitrobenzene. Other cross-linking reagents useful for this purpose include, but are not limited to: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking reagents may also be homobifunctional, i.e., having two functional groups that undergo the same reaction. A preferred homobifunctional cross-linking reagent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking reagents may also be heterobifunctional. Heterobifunctional cross-linking agents have two different functional groups, for example an amine-reactive group and a thiol-reactive group, that will cross-link two proteins having free amines and thiols, respectively. Non-limiting examples of heterobifunctional cross-linking agents are Succinimidyl-4-(N-maleimidomethyl)-cyclohexane-1-carboxylate (SMCC), m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue. Because cross-linking reagents often have low solubility in water, a hydrophilic moiety, such as a sulfonate group, may be added to the cross-linking reagent to improve its water solubility. Sulfo-MBS and sulfo-SMCC are examples of cross-linking reagents modified for water solubility. Many cross-linking reagents yield a conjugate that is essentially non-cleavable under cellular conditions, which would not be preferred. Therefore, some cross-linking reagents contain a covalent bond, such as a disulfide, that is cleavable under cellular conditions. For example, Traut's reagent, dithiobis(succinimidylpropionate) (DSP), and N-succinimidyl 3-(2-pyridyldithio)propionate (SPDP) are well-known cleavable cross-linkers. The use of a cleavable cross-linking reagent permits the cargo moiety, e.g., BAM, to separate from the novel transporter moiety after delivery into the target cell. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g., proline. Alternatively, a spacer arm may be part of the cross-linking reagent, such as in "long-chain SPDP" (e.g., Pierce Chem. Co., Rockford, Ill., cat. No. 21651 H). Numerous cross-linking reagents, including the ones discussed above, are commercially available. Detailed instructions for their use are readily available from the commercial suppliers. A general reference on protein cross-linking and conjugate preparation is Wong, *Chemistry of Protein Conjugation and Cross-Linking*, CRC Press (1991).

It will be appreciated that the different components of the BAM-conjugate molecule should be coupled in a manner so that the different components can still convey at least part of their individual activity and/or properties to the entire transporter cargo conjugate molecule. For example, coupling of the components shall preferably not lead to a total loss in targeting to C6S.

6.6.2 The BAM Moiety

The invention encompasses any BAM known or expected to be a therapeutically active component for the treatment or prevention of a disease, disorder or condition, or amelioration of a symptom thereof, e.g., such as chemical compounds, proteins, liposomes, nanoparticles and (poly-)peptides. Additionally or alternately, the BAM may be a detectable marker of use in the diagnosis of a disease or condition such as a fluorescent dye, a radioactive label or a chemoluminesent group.

Cytotoxic Drugs

Preferably the BAM of the "BAM-conjugate" of the invention is a pharmaceutical drug, e.g., selected from cytotoxic or anti-tumor drugs which are suitable as a chemotherapy drug. In general, chemotherapy drugs suitable for component (B) can be divided into three main categories based on their mechanism of action. They may (a) stop the synthesis of preDNA molecule building blocks. These agents work in a number of different ways. DNA building blocks are folic acid, heterocyclic bases, and nucleotides, which are made naturally within cells. All of these agents work to block some step in the formation of nucleotides or deoxyribonucleotides (necessary for making DNA). When these steps are blocked, the nucleotides, which are the building blocks of DNA and RNA, cannot be synthesized. Thus the cells cannot replicate because they cannot make DNA without the nucleotides. Examples of drugs in this class include methotrexate (Abitrexate®), fluorouracil (Adrucil®), hydroxyurea (Hydrea®), and mercaptopurine (Purinethol®), thioguanine, tocoferol, or, more generally, any nucleotide analogue, e.g., 2'-deoxycytidine analogues;

(b) directly damage the DNA in the nucleus of the cell. These agents chemically damage DNA and RNA. They disrupt replication of the DNA and either totally halt replication or cause the manufacture of nonsense DNA or RNA (i.e., the new DNA or RNA does not code for anything useful). Examples of drugs in this class include cisplatin (Platinol®) and antibiotics—daunorubicin (Cerubidine®), doxorubicin (Adriamycin®) belonging to the class of anthracycline antitumor agents and etoposide (VePesid®) or any intercalator; further included are radionuclides (e.g., alpha-radionucleids) commonly used in target cancer treatment (e.g., Bismuth-213); or (c) effect the synthesis or breakdown of the mitotic spindles. Mitotic spindles serve as molecular railroads with "North and South Poles" in the cell when a cell starts to divide itself into two new cells. These spindles are very important because they help to split the newly copied DNA such that a copy goes to each of the two new cells during cell division. These drugs disrupt the formation of these spindles and therefore interrupt cell division. Examples of drugs in this class of mitotic disrupters include: Vinblastine (Velban®), Vincristine (Oncovin®) and Paclitaxel (Taxol®).

The BAM of the "BAM-conjugate" of the invention may act according to one of the above modes of action. In other terms, each of the classes of anti-tumor drugs, i.e., alkylating agents, nitrosoureas, antimetabolites, plant alkaloids, anti-tumor antibiotics, and steroid hormones may be used as component the BAM of the inventive transporter cargo conjugate molecule. To describe these drug classes in more detail it is emphasized that each anti-cancer drug may also be categorized according to its effect on the cell cycle and cell chemistry as disclosed above. For example, alkylating agents kill cells by directly attacking DNA.

Alkylating agents may be used, in particular, in the treatment of chronic diseases by targeting diseased cells, e.g., in the treatment of cancers. Cyclophosphamide is an example of a commonly used alkylating agent. Nitrosoureas act similarly to alkylating agents and also inhibit changes necessary for DNA repair. These agents cross the blood-brain barrier and are therefore used to treat brain tumors, lymphomas, multiple myeloma, and malignant melanoma. Carmustine and lomustine are the major drugs in this category. Antimetabolites are drugs that block cell growth by interfering with certain activities, usually DNA synthesis. Once ingested into the cell they halt normal development and reproduction. All drugs in this category affect the cell during the "S" phase of the cell cycle. Antimetabolites may be used in the treatment of acute and chronic cancers. Nonlimiting examples of commonly used antimetabolites are 6-mercaptopurine and 5-fluorouracil (5FU). Antitumor antibiotics are a diverse group of compounds. In general, they act by binding with DNA and preventing RNA synthesis. These agents are widely used in the treatment of a variety of cancers. The most commonly used drugs in this group are doxorubicin (Adriamycin), mitomycin-C, and bleomycin. Plant (vinca) alkaloids are anti-tumor agents derived from plants. These drugs act specifically by blocking cell division during mitosis. Steroid hormones may also be useful in treating some types of tumors. This class includes adrenocorticosteroids, estrogens, antiestrogens, progesterones, and androgens. Although their specific mechanism of action is not clear, steroid hormones modify the growth of certain hormone-dependent cancers. Tamoxifen is an example, which is used for estrogen dependent breast cancer. All of the above-mentioned tumor species may be treated by the inventive BAM-conjugate molecules comprising as the BAM any of the above antitumor agents.

One group of cytotoxic or anti-tumor drugs, which may be used as the BAM component of the "BAM-conjugate" of the invention is selected from alkylating drugs, antimetabolica, cytostatics or drugs related to hormone treatment. In this context, it is preferred to select as cytotoxic or anti-tumor drugs compounds of metal, in particular platin (derivative) and taxol classes. In particular, the drug moiety is selected from the group of drugs consisting of, for example, cisplatin, transplatin, satraplatin, oxaliplatin, carboplatin, nedaplatin, chlorambucil, cyclophosphamide, mephalan, azath ioprin, fluorouracil, (6)-mercaptopurine, methorexate, nandrolone, aminogluthemide, medroxyprogesteron, megestrolacetate, procarbazin, docetaxel, paclitaxel, irinotecan, epipodophyllotoxin, podophyllotoxin, vincristine, vinblastine, docetaxel, daunomycin, daunorubicin, doxorubicin, mitoxantrone, topotecan, bleomycin, gemcitabine, fludarabine, navelbine and 5-FUDR. Particularly preferred is the class of metal-containing anticancer drugs, e.g., the class of platinum compounds.

Further cytotoxic or anti-tumor drugs, which may be used as the BAM component of the "BAM-conjugate" of the invention are Alitretinoin, Altretamine, Azathioprine, Bicalutamide, Busulfan, Bortezomib, Capecitabine, Carfilzomib, Cyclophosphamide, Exemestane, Letrozole, Finasteride, Fostamatinib, Gefitinib, Imatinib, Lenalidomide, Marizomib, Megestrol Acetate, Nilotinib, Triptorelin, Temozolomide, Mifepristone, Tretinoin, Tamoxifen, Teniposide, Peplomycin sulfate or the class of camptothecins.

Further cytotoxic or anti-tumor drugs that may be used as the BAM component of the "BAM-conjugate" of the invention are radionuclides (e.g., alpha particle emitting radionucleids) such as those commonly used in target cancer therapies well known in the art. Non-limiting examples of such radionucleids that may be of use according to the invention include Molybdenum-99, Technetium-99m, Bismuth-213, Chromium-51, Cobalt-60, Copper-64, Dysprosium-165, Erbium-169, Holmium-166, Iodine-125, Iodine-131, Iridium-192, Iron-59, Lutetium-177, Palladium-103, Phosphorus-32, Potassium-42, Rhenium-186, Rhenium-188, Samarium-153, Selenium-75, Sodium-24, Strontium-89, Xenon-133, Ytterbium-169, Ytterbium-177, Yttrium-90, Radioisotopes of caesium, gold and ruthenium. Also included are Cyclotron Radioisotopes such as Carbon-11, Nitrogen-13, Oxygen-15, Fluorine-18, Cobalt-57, Gallium-67, Indium-111, Iodine-123, Krypton-81 m, Rubidium-82, Strontium-92, Thallium-201. Alternatively or additionally, any of the above non-limiting examples may also be implemented for diagnostic or imaging uses.

Another group of cytotoxic or anti-tumor drugs, which may be used as the BAM component of the "BAM-conjugate" of the invention are indolocarbazole compounds, e.g, staurosporin (and its analogues) and rebeccamycin. It is to be mentioned that compounds belonging to the class of anilinoquinazolines (e.g., gefitinib) are also particularly preferred as the BAM component of the BAM-conjugates of the invention.

A further group of cytotoxic or anti-tumor drugs, which may be used as the BAM component of the "BAM-conjugate" of the invention may be selected from inhibitors of topoisomerases, such as irinotecan, or mitotic kinesins or DHFR.

Additionally, cytotoxic or anti-tumor drugs, which may be used as the BAM component of the "BAM-conjugate" of the invention can be selected from factors inhibiting or stimulating cell proliferation (PDGF), intracellular pathways, e.g., the RAS/RAF signaling pathway, such as a member of the RAF/MEK/ERK signaling pathway (e.g., RAF-1) or mitogen-activated protein kinase pathway, CMGC kinase family (containing CDK (cyclin dependent-kinases), MAPK, GSK3, CLK), Ser/Thr kinases that belong to the AGC kinase family containing PKA, PKG, PKC kinase families, receptor tyrosine kinases involved, e.g., in neovascularization and tumor progression, including vascular endothelial growth factor receptor (VEGFR)-2, VEGFR-3, platelet-derived growth factor receptor R, Flt-3, the endothelin (ET) system, that includes ET-1, ET-2, ET-3, and the $ET_A$ receptor ($ET_{AR}$) and $ET_{BR}$, and c-KIT, which are targeted by, e.g., inhibiting their function, and members of the IGF-family, such as IGF-1, IGF-2, IGF-1 R, IGF2R, etc.

Another group of cytotoxic or anti-tumor drugs, which may be used as the BAM component of the "BAM-transporter conjugate" of the invention may be selected from inhibitors that target tumor cell proliferation and tumor angiogenesis. Particularly preferred in this context are small molecule antitumor kinase inhibitors directed toward targets on malignant cells and/or vascular cells have antiangiogenic activity. Kinase inhibitors such as those directed toward EGFR, Her2/neu, BCR-ABL, c-KIT, PKC, Raf and PI3, are antiangiogenic by virtue of blocking secretion of angiogenic factors by affected malignant cells. Kinase inhibitors such as those directed toward VEGFR2, VEGFR1, PDGFR, PKC, Raf and PI3, are antiangiogenic by effects on vascular cells. Examples of synthetic inhibitors of cyclin dependent kinases (CDKIs) are, e.g., olomoucine, flavopiridol, butyrolactone and their derivatives and thus constrain tumor cell proliferation. On the other hand, antitumor compounds suitable as the BAM component of the inventive peptide-conjugate/BAM-conjugate molecule may be selected from activators of apoptosis programs in cancer cells (e.g., staurosporine) or by down-regulating antiapoptotic proteins, e.g., Bcl-2.

6.7 The Freely-Selectable Positions

As detailed herein, when the consensus structure of the molecule or compound of the invention according to structures (iii) to (vi) consists of or comprises exclusively amino acid residues, the targeting moiety that specifically interacts with C6S is represented by the sequence

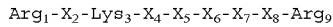

$$Arg_1\text{-}X_2\text{-}Lys_3\text{-}X_4\text{-}X_5\text{-}X_6\text{-}X_7\text{-}X_8\text{-}Arg_9$$

where $X_5$ or $X_7$ (but not both) is an arginine or a lysine residue (SEQ ID NO:5, where a fragment of SEQ ID NO:1 or SEQ ID NO:3; SEQ ID NO:6, where a fragment of SEQ ID NO:2 or SEQ ID NO:4).

As detailed herein, positions 2, 4, 6, 8 and 7 (where position 5 is defined as the arginine or lysine according to the rules set forth herein) or 5 (where position 7 is defined as the arginine or lysine according to the rules set forth herein) have little effect on specific binding of the compounds of the invention to a C6S proteoglycan; thus these positions are referenced herein as freely selectable. Use of the charged amino acids arginine or lysine is avoided in these positions, as the charged residues tend to increase the probability of non-specific interactions with proteoglycans in general.

Additionally, it is believed that the targeting moieties exhibit specificity for C6S due to the optimal linear arrangement of the arginines at positions 1 and 9, the lysine at position 3, and the lysine or arginine at position 5 or 7. Therefore, the remaining amino acids are preferably selected so as to avoid the induction of alternate 3-dimensional structures such as, e.g., α-helices. The propensity for α-helix formation for each of the naturally occurring peptidic amino acids is known, e.g., as set forth in Chakrabartty et al., *Protein Sci.* 3(1994), 843-852. The ranking from highest to lowest α-helix potential is as follows:

$$Ala > Arg^+ > Leu > Lys^+ > Glu^\circ > Met > Gln > Glu^- > Ile > Tyr > His^\circ > Ser > Cys > Asn > Asp^- > Asp > Trp > Phe > Val > Thr > His^+ > Gly > Pro.$$

Thus, it is preferred that no more than 3 amino acids with a high probability of forming an α-helix are used in the freely selectable positions. Accordingly, in preferred embodiments, no more than 3 alanines are used in the freely selectable positions. In additional or alternative further preferred embodiments, proline is not to be used in the freely selectable position.

Further it is preferred that the freely selectable positions are bulky and/or hydrophobic amino acids, as such amino acids may aid membrane insertion and cell penetration (see, e.g., Rothbard, *Cell-Penetrating Peptides: Processes and Applications*. Lanel Ü (Ed), CRC Press (2000)). Thus, in preferred embodiments wherein the molecule or compound of the invention consists or comprises a sequence according to consensus sequences (i) or (ii), the freely selectable positions are independently selected from Phe, Trp, Tyr, Val, Met, Ile and Leu. It is also known that D-amino acids enhance resistance to proteases and/or other means of protein degradation. Thus, in further preferred embodiments, which may be combined with any other embodiment disclosed herein (whether preferred or not), position 4 or position 6, or amino acid residues in residue-spacer constructs that occur at positions corresponding to these is a D-amino acid. For example, in the consensus sequences (iii) to (vi), the position corresponding to position 4 or 6 of consensus sequences (i) and (ii) is the first residue of ($SP_B$).

It is also noted that the consensus sequence of the compounds of the invention contains optional amino acid residues that act as a proton sponge. In the consensus sequences (i) to (xiv), $(XD_{11})_m$ or $(XD_{-2})_m$ and $(LD_{10})_n$ or $(LD_{-1})_n$, wherein m is 0 or 1 and n is 0-10, represent the optional proton sponge amino acids. The residues of the proton sponge may be selected from among any residue or combination of residues that is(are) known in the art or described herein capable of acting as a proton sponge. In preferred embodiments, $XD_{11}$ or $XD_{-2}$ (if the residue is present) represents any D-amino acid other than D-arginine or D-lysine and $LD_{10}$ or $LD_{-1}$ (if the residue(s) are present) represents any L- or D-amino acid other than L- or D-arginine or L- or D-lysine. In the most preferred embodiments, $XD_9$ or $XD_{-2}$ (if the residue is present) represents D-histidine, and $LD_{10}$ or $LD_{-1}$ (if the residue(s) are present) represents L- or D-histidine. As is recognized in the art, the accumulation of specific amino acid residues (e.g., histidine) inside acidic vesicles such as an endosome produces the protein sponge effect. For example, the imidazole ring of histidine is a weak base that has the ability to acquire a cationic charge when the pH of the environment drops below 6, which may further promote membrane fusion and endosome escape.

It is expressly contemplated that the embodiments described in this section and throughout this application, whether identified as preferred (including most preferred) or not, can be independently implemented or can be combined with the other disclosed embodiments in the design or selection of a compound of the invention. Therefore, the consensus sequence and/or targeting moiety of the compound may optionally satisfy none, one, or more than one of the embodiments outlined in this section and/or throughout the description. As a non-limiting example of such combination, the freely selectable positions may each be independently selected from Phe, Trp, Tyr, Val, Met, Ile and Leu, position 4 may be a D-amino acid, n of $(LD_{10})_n$ may be 0 and m of $(XD_{11})_m$ may be 1.

The novel D/L amino acid configuration and/or novel combination of chemical linkers/spacers and/or combination of the compounds of the invention allow a skilled person to define the in vivo or in vitro persistence of the inventive molecule or compound as defined above in the cell, specifically, with a half-life that closely matches the half-life of, e.g., the BAM to be administered into the cell or nucleus prior to degradation of the transporter construct by proteases.

In the context of the present invention, variants and/or fragments of peptides and/or polypeptides preferably comprise or consist of a (poly-)peptide sequence having at least 10%, 20%, 30%, 40%, 50%, 60%, 70%, 80%, or 85%, preferably at least 90%, more preferably at least 95% and most preferably at least 99% sequence identity over the whole length to the sequence of the (poly-)peptides expressly disclosed herein and subject to the rules for selection of the consensus sequence(s).

6.8 Use of Compounds of the Invention

The consensus sequences (i) to (xiv) of the invention are envisioned as transporter moieties that effect transport across the cell membrane and into the cytoplasm and/or nucleus of a cell. It is common to all of the therapeutic compounds (i.e., BAMs) disclosed herein that they have to cross the cell membrane in order to achieve therapeutic effect. By coupling compounds belonging to these classes (compounds directly damaging the DNA in the nucleus of the cell, effecting the synthesis or breakdown of the mitotic spindles or stopping the synthesis of pre-DNA molecule building blocks, or having other therapeutic effects) to the consensus sequences (i) to (x) of the invention, the entry of the BAM moieties into the cell is enhanced and/or their solubility is enhanced, thereby increasing the efficacy of these therapeutic compounds. In turn, increased cell take-up and, preferably, better solubility of these compounds in the aqueous environment (e.g., the cytosol) allows to lower the dosage of the therapeutic anti-cancer compound may be achieved.

The consensus sequences of the targeting moieties of the compounds of the invention target, in particular, the C6S proteoglycan. These proteoglycans are preferentially expressed in conjunction with the surface proteins expressed in heart, ovary, testis and central nervous system cells. Accordingly, the molecules and compounds of the invention allow the specific targeting of such cell types. Therefore, the molecules, compounds and methods of the invention facilitate the efficient delivery of cargo moieties, e.g., BAMs, to heart, ovary, testis and central nervous system cells and provide a general means of selectively delivering a substance of interest into these cells. Thus, it is preferred that the BAM to be conjugated to the transporter moiety be any substance the person skilled in the art knows or expects to exert an effect on the activity of such cells, including therapeutic effects (such as treating, preventing, attenuating or ameliorating a disease), or for the purpose of labeling such cells, e.g., for diagnostic purposes or for purposes of scientific research. Thus, the BAM-conjugates of the invention may be used for the treatment, amelioration, prophylaxis, or diagnosis of a wide range of diseases or conditions, or the symptoms thereof, in which in which these cells and/or the tissues they comprise are pathophysiologically involved and/or have a pathophysiological involvement.

Non-limiting exemplary diseases or conditions which may be treated according to the methods of the invention and by use of the molecules and compounds disclosed herein, e.g., by targeting tissues and cells of the heart, include angina, arrhythmia, atrial fibrillation, dilated cardiomyopathy, hypertrophic cardiomyopathy, congestive heart failure, endocarditis, heart rhythm disorders, myocarditis, pericarditis, premature ventricular contractions, and Wolff-Parkinson-White syndrome.

The BAM-conjugates of the invention also preferentially target tissues and cells of the ovary and testis, and, thus, may be used for the treatment, amelioration, prophylaxis, or diagnosis of a wide range of diseases or conditions in which these tissues or cells are pathophysiologically involved and/or have a pathophysiological involvement. Non-limiting exemplary diseases or conditions which may be treated include epididymitis, orchitis, spermatocele, varicocele, male hypogonadism, testicular cancer, infertility, ovarian cyst, polycystic ovary syndrome, premature ovarian failure, and ovarian cancer.

The BAM-conjugates of the invention also preferentially target tissues and cells of the central nervous system, including glial cells, and, thus, may be used for the treatment, amelioration, prophylaxis, or diagnosis of a wide range of diseases or conditions in which these tissues or cells are pathophysiologically involved and/or have a pathophysiological involvement. Non-limiting exemplary diseases or conditions which may be treated include glial related diseases of the central and peripheral nervous system, anxiety disorders, depression, epilepsy, spinal muscular atrophy, amyotrophic lateral sclerosis, Alzheimer's disease, autism, Ataxia Telangiectasia, Niemann Pick disease Type C, cerebellar degeneration, Machado-Joseph Disease, olivopontocerebella atrophy, spinocerebella ataxias, sporadic ataxia, multiple system Atrophyatrophy, Parkinson's disease, Parkinson's syndrome, gait ataxia, herpes zoster, viral encephalitis, Japanese encephalitis, bacterial encephalitis, toxoplasmosis, malaria, amoebic meningoencephalitis, *Cryptococcus neoformans* encephalitis, Lyme disease, streptococci meningoencephalitis, staphylococci meningoencephalitis, astrocytoma, glioblastoma, oligodendroglioma, ependymoma, medulloblastoma and meningioma.

The BAM-conjugates may also be of use in the treatment of diseases or conditions involving the altered production or metabolism of proteoglycans such as C6S, such as in a C6S and KS storage disease, including but not limited to morquio syndrome.

6.9 Pharmaceutical Compositions and their Administration

The invention also relates to pharmaceutical compositions comprising the molecules and compounds of the invention, e.g., BAM-conjugates. Such compositions comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The pharmaceutical compositions also may include additional therapeutic agents for the treatment of the given disease being treated. The formulation is made to suit the mode of administration. In general, methods of administering polypeptides are well known in the art and can be applied to administration of the conjugates of the invention.

Administration is by any of the routes normally used for introducing a molecule into ultimate contact with blood or the relevant target tissue as known in the art or described herein. Suitable methods of administering such conjugates in the context of the present invention to a patient are available including oral and parenteral routes. Although more than one route can be used to administer a particular composition, a particular route can often provide a more immediate and more effective action or reaction than another route.

Preferably the BAM-conjugates of the invention are administered by parenteral modes of administration, in particular by intravenous, intraperitoneal, intramuscular, intradermal, subcutaneous intrathecal, intraocular, retrobulbar, intrapulmonary or intraarticular means. Such administration routes and appropriate formulations are generally known to those of skill in the art. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilises, thickening agents, stabilizers, and preservatives. Carrier polypeptide-target polypeptide conjugates can also be administered via liposomes.

The molecules and compounds of the invention, alone or in combination with other suitable components, can also be made into aerosol formulations (i.e., they can be "nebulised") to be administered via inhalation. Aerosol formulations can be placed into pressurized acceptable propellants, such as dichlorodifluoromethane, propane, nitrogen, and the like.

In a preferred embodiment, the pharmaceutical compositions of the invention are provided in lyophilized form to be reconstituted prior to administration. Buffers and solutions for the reconstitution of the pharmaceutical compositions may be provided along with the pharmaceutical formulation to produce aqueous compositions of the present invention for administration.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, antibacterial and antifungal agents, isotonic and absorption delaying agents and the like.

Pharmaceutically acceptable carriers are determined in part by the particular composition being administered, as well as by the particular method used to administer the composition. Accordingly, there are a wide variety of suitable formulations of pharmaceutical compositions of the present invention.

Pharmaceutically acceptable carriers and excipients are well known in the art, and one or more conjugates of the invention can be formulated into pharmaceutical compositions by well-known methods (see, e.g., *Remington: The Science and Practice of Pharmacy*, 21st edition, A. R. Gennaro, Ed., Mack Publishing Company (2005); *Pharmaceutical Formulation Development of Peptides and Proteins*, S. Frokjaer and L. Hovgaard, Eds., Taylor & Francis (2000); and *Handbook of Pharmaceutical Excipients*, 3rd edition, A. Kibbe, Ed., Pharmaceutical Press (2000)).

Pharmaceutical compositions comprising one or more BAM-conjugates of the invention are optionally tested in one or more appropriate in vitro and/or in vivo animal models of disease, to confirm efficacy, tissue metabolism, and to estimate dosages, according to methods well known in the art. Thus, it is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is determinable by one of skill in the art, without undue experimentation. The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

The dose administered to a patient, in the context of the present invention, is sufficient to effect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the BAM polypeptide conjugate employed and the condition of the patient, as well as the body weight or surface area of the patient to be treated. The size of the dose is also determined by the existence, nature, and extent of any adverse side-effects that accompany the administration of a particular composition/formulation, or the like in a particular patient.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

7. EXAMPLES

7.1 Modeling Binding of TAT Peptides to C6S

Approximation of the TAT peptide interaction with C6S was performed by computer-aided modeling. The simulation modeled the TAT peptide and C6S molecules in extended conformation. It was hypothesized that the residues of TAT corresponding to positions 3, 5 or 7 and 9 of a 9-mer peptide according to the invention (e.g., according to the sequence Arg1-X2-Lys3-X4X5-X6-X7-X8-Arg9 (SEQ ID NO:5, where a fragment of SEQ ID NO:1 or SEQ ID NO:3; SEQ ID NO:6, where a fragment of SEQ ID NO:2 or SEQ ID NO:4) were spaced at favorable intervals to optimally interact with the repeating sulfates of C6S. In particular, initial comparison of the 3D structures of a TAT peptide according to the invention and C6S, in their extended conformations, revealed that the average distance between side chains of n and n+2 of a TAT peptide are very close to that of the repeating sulfates of residues n and n+2 of C6S; see, e.g., (FIG. 1 and FIG. 2).

Additional studies revealed that TAT and C6S likely bind due to the favorable electrostatic interactions between the pair of residues 1/n; 3/n+1 and n+2; 5 or 7/n+3 and n+4; and 9/n+5 and n+6 of TAT and C6S (in the recited A/B pairs, A and B designate residues of TAT and C6S, respectively); see, e.g., FIG. 1 and FIG. 2, providing schematics of TAT and C6S molecules wherein the residues are indicated according to the numbering used herein (see, also FIGS. 3 and 4, providing enlarged schematics of the TAT peptide and C6S molecule (in part) of FIGS. 1 and 2). The favorable interactions between these sets of residues may be explained by 2 mechanisms (which are not necessarily mutually exclusive), depending on whether Arg1 of TAT would bind to a sugar moiety bearing a sulfate or a carboxylate group.

Due to the nature, the size and the flexibility of the two partners, it was not possible to identify the most likely binding mode using docking software. Therefore, the following strategy was implemented: (i) extended 3D conformers of both molecules were used as starting input; (ii) the molecules were manually positioned to form the 3 adjacent contacts as described above (e.g. 3/n+1, 5 or 7/n+3, and 9/n+5); (iii) a total of 600 ns of Molecular Dynamics (MD) simulations at 300 K was performed while maintaining the chosen triplet of interactions; and, eventually, (iv) determining whether new interactions would emerge during the MD simulations, and at which frequency. Importantly, at the start of the MD simulation, no interactions other than the chosen starting interactions occur between TAT and C6S.

The reasoning supporting this approach is that, if the envisioned interaction scheme constituted by the four major pairs of interacting residues is correct, and if, for instance residue 3 of TAT binds preferably to a sulfated moiety of C6S, then, a MD simulation starting from a complex with only an interacting triplet (e.g., 1/n, 3/n+1 and 5/n+3) should lead to the spontaneous formation of the additional interactions, e.g., 9/n+5, but only if residue n+1 of C6S is a sulfated residue.

The interactions between TAT and C6S were modeled using the GROMACS molecular modeling package. The TAT peptide (sequence: RKKRRQRR (SEQ ID NO:25)) was described using the CHARMM22 all-hydrogen force fields (Mackerell et al., *J. Phsy. Chem. B* 102(1998), 3586-3616), while topology and parameters were obtained using SwissParam for the C6S molecule, see, e.g., Zoete et al., *J. Comput. Chem.* 32(2011), 2359-2368. The C6S molecule was modeled to contain 10 sugar moieties, as schematically represented in FIGS. 1 and 2.

The starting points of the MD simulation were generated by manually positioning TAT and C6S to form the interaction schemes of interest, i.e., involving three residues of C6S and 3 residues of TAT, e.g., residues 1,3,5 or 3,5,9. To maintain the interaction between the chosen TAT/C6S residue pairs during the MD simulation, a "NOE" distance restraint was applied to them, with minimal and maximal distances of 5 and 7 Å, respectively; and a constant force set at 1000 kcal mol$^{-1}$ Å$^{-2}$. The system was then minimized using 5000 steps of ABNR. Finally, for each starting interaction scheme, a pool of 30 independent MD simulations, each 20 ns in length, was performed at 300K to check whether additional interactions would take place between C6S and TAT. The solvent effect was estimated using a Generalized Born implicit solvation model, with a dielectric constant of 1 for the solute and 80 for the solvent. For each MD simulation, 1000 frames, regularly separated, were extracted from the trajectory file. For each frame, pairs of interacting residues were identified as those having heavy atoms at a distance smaller than 5 Å. Finally, the frequency of existence of each possible pair of interacting residues was averaged over all frames extracted from the 30 MD simulations of each pool.

Several simulations were performed, each using different starting interaction schemes. In all cases where the scheme involved the interaction of residue 3 of TAT with a sulfated residue of C6S, nearly all the interactions expected according to our above-mentioned hypothesis occurred spontaneously during the MD simulation. In contrast, the expected interactions did not occur when the starting scheme involved an interaction between residue 3 of TAT and a carboxylated C6S residue. The results of the simulations support the hypothesis that TAT and C6S interact due to favorable electrostatic interactions between the pair of residues 1/n; 3/n+1 and n+2; 5 or 7/n+3 and n+4; and 9/n+5, respectively, where residue n of C6S is a carboxylated moiety.

As predicted by the model results described above, the simulation results indicated that residues at positions 3, 5 or 7, and 9 of the nine-mer peptides according to the invention exhibited favorable interactions with the sulfated residues on the sugars of C6S. Additionally, the residue at position 1 of the nine-mer peptide was predicted able to interact with the carboxylate on the sugar at positions n of the C6S.

7.2 Binding of TAT Peptides to C6S Evaluated by ELISA

Figure 5A:
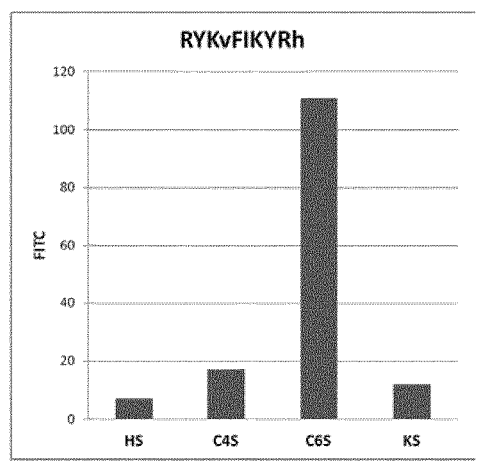
Figure 5B:
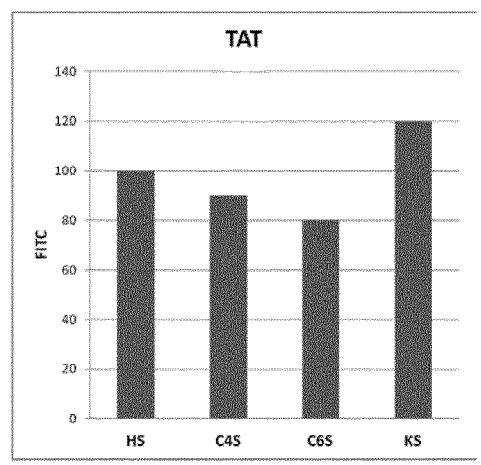

The binding of the nine-mer peptides of the invention to C6S as predicted by the models, in particular, as compared to the binding to other proteoglycans was tested using a modified ELISA protocol. ELISA plates were coated overnight with 1 mg/ml of heparin sulfate (HS), chondroitin-4-sulfate (C4S), chondroitin-6-sulfate (C6S) or keratin sulfate (KS) in PBS. The wells were then washed with PBS and incubated for 1 hour at room temperature with 1 mg/ml of an exemplary peptide of the invention having the sequence RYKvFIKYRh ("RYK-C6S"; SEQ ID NO:7) or a standard TAT peptide. The plates were then thoroughly washed with PBS and subsequently photographed with a LUMAS-COPE™ luminescent microscope. Images were then quantified using the ImageJ software (FIG. 5). The results presented in FIG. 5 demonstrate, that in contrast to the standard TAT peptide (FIG. 5B), the RYK-C6S peptide (SEQ ID NO:7) according to the invention specifically binds to the C6S proteoglycan, and in particular, selectively binds C6S over the other proteoglycans tested (FIG. 5A).

Figure 6A:
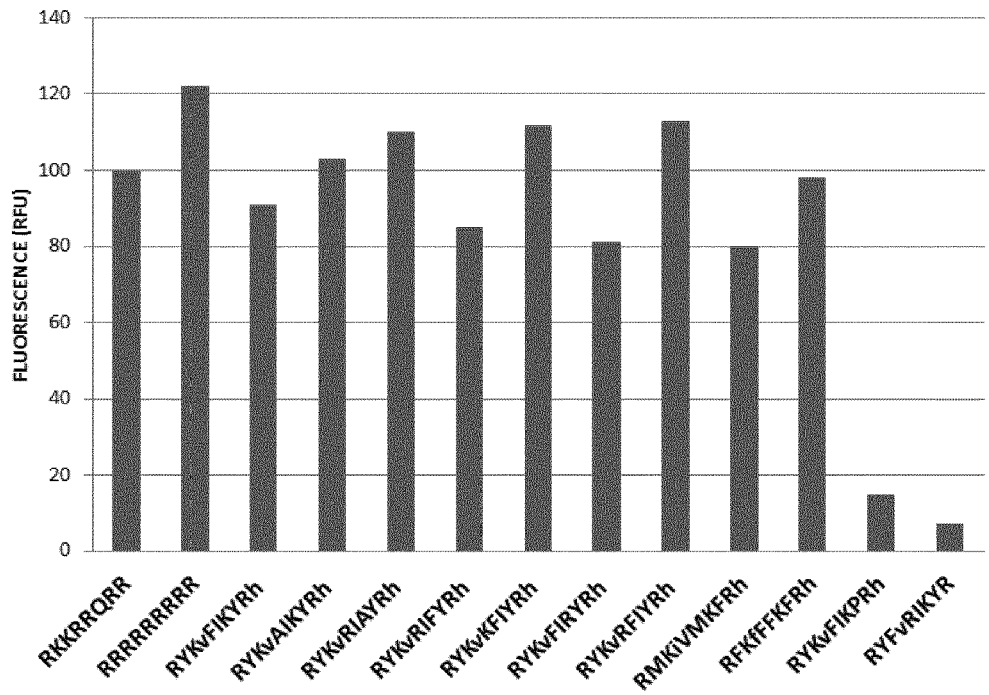

The same modified ELISA protocol was used to examine the impact on the specific binding to C6S by modifying the freely-selectable positions 2, 4, 6, 8 and (5 or 7). FIG. 6A demonstrates that the amino acid residue at these positions had little impact on specific binding, but that, as expected, the presence of positively charged residues, e.g., arginine and/or lysine, at these positions correlated with increases in binding that were likely non-selective and due to non-specific interactions; see, e.g., FIG. 6A, the binding of the standard TAT peptide RKKRRQRR (SEQ ID NO:25) and pure arginine 9-mer, RRRRRRRRR (SEQ ID NO:26). Additionally, the use of proline at position 8 eliminated binding activity in at least one peptide tested; see, FIG. 6A, the binding of RYKvFIKPRh (SEQ ID NO:27). Similarly, deviation from the consensus sequence as defined herein eliminated binding; specifically, replacement of Lys3 with a Phe reside eliminated binding to C6S; see, FIG. 6A, the binding of RYFvRIKYR (SEQ ID NO:28).

Figure 6B:
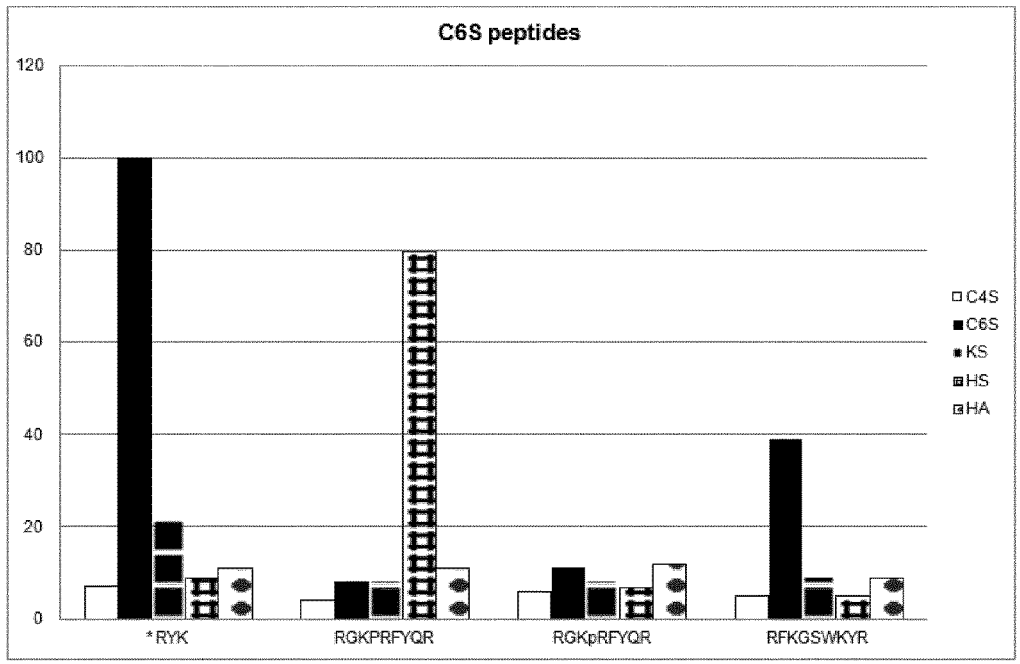

The impact of sequence variation on specific binding was also investigated with select peptides using the above described modified ELISA. As seen in FIG. 6B, the control consensus peptide of the invention "RYK" (referenced as "RYK-C6S in FIG. 6A, RYKvFIKYRh; SEQ ID NO:7) exhibited strong and selective binding to C6S. FIG. 6B also demonstrates that the use of proline in the consensus sequence either eliminated binding activity to any proteoglycan or eliminated the specificity to C6S, see, FIG. 6B, the binding of an 11-mer peptide comprising the consensus sequence RGKPRFYQR (SEQ ID NO:31) and the same 11-mer peptide replacing the L-proline residue with its D-counterpart, i.e., comprising the consensus sequence RGKpRFYQR (SEQ ID NO:32). FIG. 6B also demonstrates that 9-mer peptide RFKGSWKYR (SEQ ID NO:33) exhibited specific and selective binding for C6S.

7.3 Tissue Expression of Genes Involved in Production of C6S

The genes CHST3 and CHST7 are the primary genes involved in the sulfation of chondroitin to produce chondroitin-6-sulfate. Expression data from Atlas arrays revealed that the CHST3 and CHST7 genes are preferentially expressed in cells of the ovary, heart and testis; see, FIGS. 7 and 8, respectively. CHST3 gene expression is increased in injured central nervous system and chondroitin-6-sulfate synthesis is upregulated; see, e.g., Properzi et al., *Eur. J. Neurosci.* 21(2005), 378-390. Accordingly, the peptides and methods of the invention preferentially allow the targeting of these tissues and the treatment of diseases or conditions wherein these cells have pathophysiological involvement.

7.4 In Vitro Activity of Consensus Sequence Peptides

The activity of peptides of the invention as targeting moieties was tested in vitro in preliminary studies using cells lines expressing C6S. The nucleoside analog 3' amino deoxythymidine (3'AdT) was conjugated to the amino-terminus of the peptide "RYK" (RYKvFIKYRh (SEQ ID NO:8)) using a single D-Glu residue (3'AdT-e-RYK). Previous work (data not shown) revealed that 3'AdT was inactive as a cytostatic when added alone to culture medium.

Confluent cultures of MDCK were passaged at 1/20 dilution and exponentionally growing cells were incubated for 96 hours with concentrations of the nucleoside analog conjugates ranging from 0.5 µM to 10 µM. Viability was subsequently assessed using trypan blue exclusion.

FIG. 9 demonstrates a clear dose response. The D-linked conjugate had substantial effects on viability at concentrations at least ≥0.5 µM.

7.5 Estimation of In Vivo Stability

The stability of peptides of the invention was estimated by mixing the peptides with fetal calf serum and incubating at 37° C. for 6 hr. Samples were tested at both 0 and 6 hours. The peptide RFKGSWKYR (SEQ ID NO:33) was completely degraded by 6 hrs. In contrast, no degradation of the RYK peptide (RYKvFIKYRh; SEQ ID NO:8) was detected at 6 hours, i.e., it was 100% stable. The results indicate that the inclusion of a D-amino acid residue significantly improves resistance of the compound of the invention to protease activity.

---

The invention claimed is:

1. A molecule or compound comprising the consensus structure:

(I)
$Arg_1-(SP_A)-Lys_3-(SP_B)-X-(SP_C)-Arg_9-(LD_{10})_n-(XD_{11})_m$;
or (II)
$(XD_{-2})_m$-$(LD_{-1})_n$-$Arg_1$-$(SP_A)$-$Lys_3$-$(SP_C)$-X-$(SP_B)$-$Arg_9$;

(a) wherein, $LD_{10}$ or $LD_{-1}$ represents any L- or D- amino acid other than D-arginine, D-lysine; L-arginine or L-lysine and n has a value of 0 to 10;

(b) wherein $XD_{11}$ or $XD_{-2}$ represents any D-amino acid other than D-arginine or D-lysine and m has a value of 0 or 1;

(c) wherein (i) $Arg_1$ and $Arg_9$ represent L-arginine; $Lys_3$ represents L-lysine, and X represents L-arginine or L-lysine; or (ii) $Arg_1$ and $Arg_9$ represent D-arginine; $Lys_3$ represents D-lysine, and X represents D-arginine or D-lysine;

(d) wherein $(SP_A)$ represents a chemical linker that (i) consists of a single amino acid residue, which may be any L- or D- amino acid other than D-arginine, D-lysine, L-arginine or L-lysine; or (ii) does not comprise amino acid residues and separates the adjacent amino acid residues by 9.7±1.5 Å;

(e) wherein $(SP_B)$ represents a chemical linker that (i) consists of a peptide chain of 3 amino acid residues, each of which residue may be independently selected from any L- or D- amino acid other than D-arginine, D-lysine, L-arginine or L-lysine; or (ii) does not comprise amino acid residues and separates the adjacent amino acid residues by 13.3±1.5 Å;

(f) wherein $(SP_C)$ represents a chemical linker that (i) consists of a single amino acid residue, which may be any L- or D- amino acid other than D-arginine, D-lysine, L-arginine or L-lysine; or (ii) does not comprise amino acid residues and contributes to the linker $(SP_B)$-X-$(SP_C)$ such that it separates $Lys_3$ and $Arg_9$ by 18.0±1.5 Å;

(g) wherein where $(SP_A)$, $(SP_B)$ and $(SP_C)$ each represent or comprise only amino acid residues independently selected from any L- or D-amino acid residues other than D-arginine, D-Lysine, L-arginine or L-lysine; $(SP_A)$, $(SP_B)$ and $(SP_C)$ together comprise at least one L-amino acid residue and at least one D-amino acid residue;

(h) and wherein $(SP_A)$, $(SP_B)$ and $(SP_C)$ together contain no proline residues.

2. The molecule or compound according to claim 1, wherein $(SP_A)$ represents a chemical linker that separates the adjacent amino acid residues by 9.7±1.5 Å;

$(SP_B)$ represents a chemical linker that separates the adjacent amino acid residues by 13.3±1.5 Å; and $(SP_B)$-X-$(SP_C)$ represents a chemical linker that separates $Lys_3$ and $Arg_9$ by 18.0±1.5 Å.

3. The molecule or compound of claim 1, wherein one or more of said chemical linkers is a beta-peptide, a sugar-amino acid based scaffold, a beta-hairpin peptidomimetic, an alpha-helical mimetic or a cyclotide.

4. The molecule or compound of claim 1, wherein $(SP_A)$ and $(SP_C)$ each represent a single amino acid residue that is independently selected from any L- or D-amino acid residue other than D-arginine, D-lysine, L-arginine or L-lysine, wherein $(SP_B)$ represents a peptide chain consisting of 3 amino acid residues, each residue independently selected from any L- or D-amino acid residue other than D-arginine, D-lysine, L-arginine or L-lysine, and wherein $(SP_A)$, $(SP_B)$ and $(SP_C)$ together contain no proline residues.

5. The molecule or compound according to claim 1, wherein $(SP_A)$, $(SP_B)$ and $(SP_C)$ together contain no more than 3 alanine residues.

6. The molecule or compound according to claim 1, wherein neither $LD_{10}$ nor $LD_{-1}$ represents or comprises a proline residue.

7. The molecule or compound according to claim 1 wherein one or more of $(SP_A)$, $(SP_B)$ and $(SP_C)$ includes one or more amino acids selected from Ile, Tyr, Phe, Trp, Val, Met, and Leu.

8. The molecule or compound according to claim 1, wherein the first amino acid of $(SP_B)$ is a D-amino acid.

9. The molecule or compound according to claim 1, wherein $LD_{10}$ or $LD_{-1}$ represents L- or D-histidine.

10. The molecule or compound according to claim 1, wherein $XD_{11}$ or $XD_{-2}$ represents D-histidine.

11. The molecule or compound according to claim 1, wherein m has a value of 1 and/or n has a value of 0.

12. The molecule or compound according to claim 1 comprising a sequence selected from the group consisting of:

```
                                    (SEQ ID NO: 7)
RYKITIKYR (SEQ ID NO: 8)
RYKITIKYRh (SEQ ID NO: 9)
RYKvAIKYR (SEQ ID NO: 10)
RYKvAIKYRh (SEQ ID NO: 17)
RYKvFIRYR (SEQ ID NO: 18)
RYKvFIRYRh (SEQ ID NO: 21)
RIVIKiVMKFR (SEQ ID NO: 22)
RIVIKiVMKFRh (SEQ ID NO: 23)
RFKfFFKFR
and (SEQ ID NO: 24)
RFKfFFKFRh.
```

13. A conjugate of a biologically active moiety (BAM) and a consensus structure, wherein said BAM is conjugated to the terminus of said consensus structure, and wherein said consensus structure is a molecule or compound having a consensus structure according to one of the following:

```
(III)
(BAM)-(LINK)-Arg₁-(SP_A)-Lys₃-(SP_B)-X-(SP_C)-Arg₉-
(LD₁₀)_n-(XD₁₁)_m;
or
(IV)
(XD₋₂)_m-(LD₋₁)_n-Arg₁-(SP_A)-Lys₃-(SP_B)-X-(SP_C)-Arg₉-
(LINK)-(BAM)
```

(a) wherein (BAM) represents a biologically active moiety;

(b) wherein (LINK) represents an optional linker group;

(c) wherein, $LD_{10}$ or $LD_{-1}$ represents any L- or D- amino acid other than D-arginine, D-lysine; L-arginine or L-lysine and n has a value of 0 to 10;

(d) wherein $XD_{11}$ or $XD_{-2}$ represents any D-amino acid other than D-arginine or D-lysine and m has a value of 0 or 1;

(e) wherein
  (i) $Arg_1$ and $Arg_9$ represent L-arginine; $Lys_3$ represents L-lysine, and X represents L-arginine or L-lysine; or
  (ii) $Arg_1$ and $Arg_9$ represent D-arginine; $Lys_3$ represents D-lysine, and X represents D-arginine or D-lysine;

(f) wherein ($SP_A$) represents a chemical linker that
  (i) consists of a single amino acid residue, which may be any L- or D- amino acid other than D-arginine, D-lysine, L-arginine or L-lysine; or
  (ii) does not comprise amino acid residues and separates the adjacent amino acid residues by 9.7±1.5 Å;

(g) wherein ($SP_B$) represents a chemical linker that
  (i) consists of a peptide chain of 3 amino acid residues, each of which residue may be independently selected from any L- or D- amino acid other than D-arginine, D-lysine, L-arginine or L-lysine; or
  (ii) does not comprise amino acid residues and separates the adjacent amino acid residues by 13.3±1.5 Å;

(h) wherein ($SP_C$) represents a chemical linker that
  (i) consists of a single amino acid residue, which may be any L- or D- amino acid other than D-arginine, D-lysine, L-arginine or L-lysine; or
  (ii) does not comprise amino acid residues and contributes to the linker ($SP_B$)-X-($SP_C$) such that it or its reverse, ($SP_C$)-X($SP_B$) separates $Lys_3$ and $Arg_9$ by 18.0±1.5 Å;

(i) wherein where ($SP_A$), ($SP_B$) and ($SP_C$) each represent or comprise only amino acid residues independently selected from any L- or D- amino acid residues other than D-arginine, D-Lysine, L-arginine or L-lysine; ($SP_A$), ($SP_B$) and ($SP_C$) together comprise at least one L-amino acid residue and at least one D-amino acid residue;

(j) and wherein ($SP_A$), ($SP_B$) and ($SP_C$) together contain no proline residues.

14. The conjugate of claim 13, wherein the linker group (LINK) is L- or D- Glu.

15. A pharmaceutical composition comprising the conjugate according to claim 13.

16. The conjugate of claim 13, wherein said BAM is conjugated to the $Arg_1$ by a covalent N-terminus amide- or to $Arg_9$ by a C-terminus ester bond.

17. A conjugate of a biologically active moiety (BAM) and consensus structure (I) or (II):

```
(I)
Arg₁-(SP_A)-Lys₃-(SP_B)-X-(SP_C)-Arg₉-(LD₁₀)_n-(XD₁₁)_m;
or
(II)
(XD₋₂)_m-(LD₋₁)_n-Arg₁-(SP_A)-Lys₃-(SP_B)-X-(SP_C)-Arg₉;
```

(a) wherein, $LD_{10}$ or $LD_{-1}$ represents any L- or D- amino acid other than D-arginine, D-lysine; L-arginine or L-lysine and n has a value of 0 to 10;

(b) wherein $XD_{11}$ or $XD_{-2}$ represents any D-amino acid other than D-arginine or D-lysine and m has a value of 0 or 1;

(c) wherein
  (i) $Arg_1$ and $Arg_9$ represent L-arginine; $Lys_3$ represents L-lysine, and X represents L-arginine or L-lysine; or
  (ii) $Arg_1$ and $Arg_9$ represent D-arginine; $Lys_3$ represents D-lysine, and X represents D-arginine or D-lysine;

(d) wherein ($SP_A$) represents a chemical linker that
  (i) consists of a single amino acid residue, which may be any L- or D- amino acid other than D-arginine, D-lysine, L-arginine or L-lysine; or
  (ii) does not comprise amino acid residues and separates the adjacent amino acid residues by 9.7±1.5 Å;

(e) wherein ($SP_B$) represents a chemical linker that
  (i) consists of a peptide chain of 3 amino acid residues, each of which residue may be independently selected from any L- or D- amino acid other than D-arginine, D-lysine, L-arginine or L-lysine; or (ii) does not comprise amino acid residues and separates the adjacent amino acid residues by 13.3±1.5 Å;

(f) wherein ($SP_C$) represents a chemical linker that
   (i) consists of a single amino acid residue, which may be any L- or D- amino acid other than D-arginine, D-lysine, L-arginine or L-lysine; or
   (ii) does not comprise amino acid residues and contributes to the linker ($SP_B$)-X-($SP_C$) such that it separates $Lys_3$ and $Arg_9$ by 18.0±1.5 Å;

(g) wherein where ($SP_A$), ($SP_B$) and ($SP_C$) each represent or comprise only amino acid residues independently selected from any L- or D- amino acid residues other than D-arginine, D-Lysine, L-arginine or L-lysine; ($SP_A$), ($SP_B$) and ($SP_C$) together comprise at least one L-amino acid residue and at least one D-amino acid residue;

(h) and wherein ($SP_A$), ($SP_B$) and ($SP_C$) together contain no proline residues, wherein said BAM is conjugated to an amino acid residue and/or a chemical group of ($SP_A$), ($SP_B$), or ($SP_C$).

18. The conjugate according to claim 13 wherein the BAM is a mono- or poly-saccharide, a cytotoxic agent, an antineoplastic agent, an anti-inflammatory agent, an anti-viral agent, an anti-bacterial agent or an anti-protozoal agent.

19. The conjugate according to claim 13, wherein the BAM is deoxyribose or ribose.

20. A method of treating a heart disease or condition, a disease or condition of the ovary or testis, a disease or condition of the central nervous system, or a C6S accumulation disease comprising administering to an individual in need thereof a conjugate according to claim 13.

* * * * *

SEQUENCE LISTING

```
<160> NUMBER OF SEQ ID NOS: 33

<210> SEQ ID NO 1
<211> LENGTH: 20
<212> TYPE: PRT
<213> ORGANISM: Artificial Sequence
<220> FEATURE:
<223> OTHER INFORMATION: Artificial C6S binding protein
<220> FEATURE:
<221> NAME/KEY: VARIANT
<222> LOCATION: (2)..(2)
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: (4)..(4)
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is any L- or D- amino acid
      other than L-Lys, D-Lys, L-Arg or D-Arg, subject to the proviso
      that Xaa at position 5 or Xaa at position 7, but not both, is
      L-Lys or L-Arg
<220> FEATURE:
<221> NAME/KEY: VARIANT
<222> LOCATION: (6)..(6)
<223> OTHER INFORMATION: Xaa at position 6 is any L- or D- amino acid
      other than L-Lys, D-Lys, L-Arg or D-Arg
<220> FEATURE:
<221> NAME/KEY: VARIANT
<222> LOCATION: (7)..(7)
<223> OTHER INFORMATION: Xaa at position 7 is any L- or D- amino acid
      other than L-Lys, D-Lys, L-Arg or D-Arg, subject to the proviso
      that Xaa at position 5 or Xaa at position 7, but not both, is
      L-Lys or L-Arg
<220> FEATURE:
<221> NAME/KEY: VARIANT
<222> LOCATION: (8)..(8)
<223> OTHER INFORMATION: Xaa at position 8 is any L- or D- amino acid
      other than L-Lys, D-Lys, L-Arg or D-Arg
<220> FEATURE:
<221> NAME/KEY: VARIANT
<222> LOCATION: (10)..(10)
<223> OTHER INFORMATION: Xaa at position 10 is absent or present and may
      be any L- or D-amino acid other than L-Lys, D-Lys, L-Arg or D-Arg
<220> FEATURE:
<221> NAME/KEY: VARIANT
<222> LOCATION: (11)..(11)
<223> OTHER INFORMATION: Xaa at position 11 is absent or present and may
``` be any L- or D-amino acid other than L-Lys, D-Lys, L-Arg or D-Arg
<220> FEATURE:
<221> NAME/KEY: VARIANT
<222> LOCATION: (12)..(12)
<223> OTHER INFORMATION: Xaa at position 12 is absent or present and may
      be any L- or D-amino acid other than L-Lys, D-Lys, L-Arg or D-Arg
<220> FEATURE:
<221> NAME/KEY: VARIANT
<222> LOCATION: (13)..(13)
<223> OTHER INFORMATION: Xaa at position 13 is absent or present and may
      be any L- or D-amino acid other than L-Lys, D-Lys, L-Arg or D-Arg
<220> FEATURE:
<221> NAME/KEY: VARIANT
<222> LOCATION: (14)..(14)
<223> OTHER INFORMATION: Xaa at position 14 is absent or present and may
      be any L- or D-amino acid other than L-Lys, D-Lys, L-Arg or D-Arg
<220> FEATURE:
<221> NAME/KEY: VARIANT
<222> LOCATION: (15)..(15)
<223> OTHER INFORMATION: Xaa at position 15 is absent or present and may
      be any L- or D-amino acid other than L-Lys, D-Lys, L-Arg or D-Arg
<220> FEATURE:
<221> NAME/KEY: VARIANT
<222> LOCATION: (16)..(16)
<223> OTHER INFORMATION: Xaa at position 16 is absent or present and may
      be any L- or D-amino acid other than L-Lys, D-Lys, L-Arg or D-Arg
<220> FEATURE:
<221> NAME/KEY: VARIANT
<222> LOCATION: (17)..(17)
<223> OTHER INFORMATION: Xaa at position 17 is absent or present and may
      be any L- or D-amino acid other than L-Lys, D-Lys, L-Arg or D-Arg
<220> FEATURE:
<221> NAME/KEY: VARIANT
<222> LOCATION: (18)..(18)
<223> OTHER INFORMATION: Xaa at position 18 is absent or present and may
      be any L- or D-amino acid other than L-Lys, D-Lys, L-Arg or D-Arg
<220> FEATURE:
<221> NAME/KEY: VARIANT
<222> LOCATION: (19)..(19)
<223> OTHER INFORMATION: Xaa at position 19 is absent or present and may
      be any L- or D-amino acid other than L-Lys, D-Lys, L-Arg or D-Arg
<220> FEATURE:
<221> NAME/KEY: VARIANT
<222> LOCATION: (20)..(20)
<223> OTHER INFORMATION: Xaa at position 20 is absent or present and may
      be any  D- amino acid other than D-Arg or D-Lys

<400> SEQUENCE: 1

Arg Xaa Lys Xaa Xaa Xaa Xaa Xaa Arg Xaa Xaa Xaa Xaa Xaa Xaa Xaa
1               5                   10                  15

Xaa Xaa Xaa Xaa
            20

<210> SEQ ID NO 2
<211> LENGTH: 20
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (1)..(1)
<223> OTHER INFORMATION: Xaa at position 1 is D-Arg
<220> FEATURE:
<221> NAME/KEY: VARIANT
<222> LOCATION: (2)..(2)
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: (3)..(3)
<223> OTHER INFORMATION: Xaa at position 3 is D-Lys
<220> FEATURE:
<221> NAME/KEY: VARIANT
<222> LOCATION: (4)..(4)
<223> OTHER INFORMATION: Xaa at position 4 is any L- or D- amino acid

```
        other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is any L- or D- amino acid
        other than L-Lys, D-Lys, L-Arg or D-Arg, subject to the proviso
        that Xaa at position 5 or Xaa at position 7, but not both, is
        D-Lys or D-Arg
<220> FEATURE:
<221> NAME/KEY: VARIANT
<222> LOCATION: (6)..(6)
<223> OTHER INFORMATION: Xaa at position 6 is any L- or D- amino acid
        other than L-Lys, D-Lys, L-Arg or D-Arg
<220> FEATURE:
<221> NAME/KEY: VARIANT
<222> LOCATION: (7)..(7)
<223> OTHER INFORMATION: Xaa at position 7 is any L- or D- amino acid
        other than L-Lys, D-Lys, L-Arg or D-Arg, subject to the proviso
        that Xaa at position 5 or Xaa at position 7, but not both, is
        D-Lys or D-Arg
<220> FEATURE:
<221> NAME/KEY: VARIANT
<222> LOCATION: (8)..(8)
<223> OTHER INFORMATION: Xaa at position 8 is any L- or D- amino acid
        other than L-Lys, D-Lys, L-Arg or D-Arg
<220> FEATURE:
<221> NAME/KEY: VARIANT
<222> LOCATION: (9)..(9)
<223> OTHER INFORMATION: Xaa at position 9 is D-Arg
<220> FEATURE:
<221> NAME/KEY: VARIANT
<222> LOCATION: (10)..(10)
<223> OTHER INFORMATION: Xaa at position 10 is absent or present and may
        be any L- or D-amino acid other than L-Lys, D-Lys, L-Arg or D-Arg
<220> FEATURE:
<221> NAME/KEY: VARIANT
<222> LOCATION: (11)..(11)
<223> OTHER INFORMATION: Xaa at position 11 is absent or present and may
        be any L- or D-amino acid other than L-Lys, D-Lys, L-Arg or D-Arg
<220> FEATURE:
<221> NAME/KEY: VARIANT
<222> LOCATION: (12)..(12)
<223> OTHER INFORMATION: Xaa at position 12 is absent or present and may
        be any L- or D-amino acid other than L-Lys, D-Lys, L-Arg or D-Arg
<220> FEATURE:
<221> NAME/KEY: VARIANT
<222> LOCATION: (13)..(13)
<223> OTHER INFORMATION: Xaa at position 13 is absent or present and may
        be any L- or D-amino acid other than L-Lys, D-Lys, L-Arg or D-Arg
<220> FEATURE:
<221> NAME/KEY: VARIANT
<222> LOCATION: (14)..(14)
<223> OTHER INFORMATION: Xaa at position 14 is absent or present and may
        be any L- or D-amino acid other than L-Lys, D-Lys, L-Arg or D-Arg
<220> FEATURE:
<221> NAME/KEY: VARIANT
<222> LOCATION: (15)..(15)
<223> OTHER INFORMATION: Xaa at position 15 is absent or present and may
        be any L- or D-amino acid other than L-Lys, D-Lys, L-Arg or D-Arg
<220> FEATURE:
<221> NAME/KEY: VARIANT
<222> LOCATION: (16)..(16)
<223> OTHER INFORMATION: Xaa at position 16 is absent or present and may
        be any L- or D-amino acid other than L-Lys, D-Lys, L-Arg or D-Arg
<220> FEATURE:
<221> NAME/KEY: VARIANT
<222> LOCATION: (17)..(17)
<223> OTHER INFORMATION: Xaa at position 17 is absent or present and may
        be any L- or D-amino acid other than L-Lys, D-Lys, L-Arg or D-Arg
<220> FEATURE:
<221> NAME/KEY: VARIANT
<222> LOCATION: (18)..(18)
<223> OTHER INFORMATION: Xaa at position 18 is absent or present and may
        be any L- or D-amino acid other than L-Lys, D-Lys, L-Arg or D-Arg
<220> FEATURE:
<221> NAME/KEY: VARIANT
<222> LOCATION: (19)..(19)
<223> OTHER INFORMATION: Xaa at position 19 is absent or present and may
        be any L- or D-amino acid other than L-Lys, D-Lys, L-Arg or D-Arg
```

```
<220> FEATURE:
<221> NAME/KEY: VARIANT
<222> LOCATION: (20)..(20)
<223> OTHER INFORMATION: Xaa at position 20 is absent or present and may
      be any  D-amino acid other than D-Lys or D-Arg

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (1)..(1)
<223> OTHER INFORMATION: Xaa at position 1 is absent or present and may
      be any  D-amino acid other than D-Lys or D-Arg
<220> FEATURE:
<221> NAME/KEY: VARIANT
<222> LOCATION: (2)..(2)
<223> OTHER INFORMATION: Xaa at position 2 is absent or present and may
      be any L- or D-amino acid other than L-Lys, D-Lys, L-Arg or D-Arg
<220> FEATURE:
<221> NAME/KEY: VARIANT
<222> LOCATION: (3)..(3)
<223> OTHER INFORMATION: Xaa at position 3 is absent or present and may
      be any L- or D-amino acid other than L-Lys, D-Lys, L-Arg or D-Arg
<220> FEATURE:
<221> NAME/KEY: VARIANT
<222> LOCATION: (4)..(4)
<223> OTHER INFORMATION: Xaa at position 4 is absent or present and may
      be any L- or D-amino acid other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is absent or present and may
      be any L- or D-amino acid other than L-Lys, D-Lys, L-Arg or D-Arg
<220> FEATURE:
<221> NAME/KEY: VARIANT
<222> LOCATION: (6)..(6)
<223> OTHER INFORMATION: Xaa at position 6 is absent or present and may
      be any L- or D-amino acid other than L-Lys, D-Lys, L-Arg or D-Arg
<220> FEATURE:
<221> NAME/KEY: VARIANT
<222> LOCATION: (7)..(7)
<223> OTHER INFORMATION: Xaa at position 7 is absent or present and may
      be any L- or D-amino acid other than L-Lys, D-Lys, L-Arg or D-Arg
<220> FEATURE:
<221> NAME/KEY: VARIANT
<222> LOCATION: (8)..(8)
<223> OTHER INFORMATION: Xaa at position 8 is absent or present and may
      be any L- or D-amino acid other than L-Lys, D-Lys, L-Arg or D-Arg
<220> FEATURE:
<221> NAME/KEY: VARIANT
<222> LOCATION: (9)..(9)
<223> OTHER INFORMATION: Xaa at position 9 is absent or present and may
      be any L- or D-amino acid other than L-Lys, D-Lys, L-Arg or D-Arg
<220> FEATURE:
<221> NAME/KEY: VARIANT
<222> LOCATION: (10)..(10)
<223> OTHER INFORMATION: Xaa at position 10 is absent or present and may
      be any L- or D-amino acid other than L-Lys, D-Lys, L-Arg or D-Arg
<220> FEATURE:
<221> NAME/KEY: VARIANT
<222> LOCATION: (11)..(11)
<223> OTHER INFORMATION: Xaa at position 11 is absent or present and may
      be any L- or D-amino acid other than L-Lys, D-Lys, L-Arg or D-Arg
<220> FEATURE:
<221> NAME/KEY: VARIANT
<222> LOCATION: (13)..(13)
```

```
<223> OTHER INFORMATION: Xaa at position 13 is any L- or D- amino acid
      other than L-Lys, D-Lys, L-Arg or D-Arg
<220> FEATURE:
<221> NAME/KEY: VARIANT
<222> LOCATION: (15)..(15)
<223> OTHER INFORMATION: Xaa at position 15 is any L- or D- amino acid
      other than L-Lys, D-Lys, L-Arg or D-Arg
<220> FEATURE:
<221> NAME/KEY: VARIANT
<222> LOCATION: (16)..(16)
<223> OTHER INFORMATION: Xaa at position 16 is any L- or D-amino acid
      other than L-Lys, D-Lys, L-Arg, or D-Arg, subject to the proviso
      that Xaa at position 16 or Xaa at position 18, but not both, is
      L-Lys or L-Arg
<220> FEATURE:
<221> NAME/KEY: VARIANT
<222> LOCATION: (17)..(17)
<223> OTHER INFORMATION: Xaa at position 17 is any L- or D- amino acid
      other than L-Lys, D-Lys, L-Arg or D-Arg
<220> FEATURE:
<221> NAME/KEY: VARIANT
<222> LOCATION: (18)..(18)
<223> OTHER INFORMATION: Xaa at position 18 is any L- or D-amino acid
      other than L-Lys, D-Lys, L-Arg, or D-Arg, subject to the proviso
      that Xaa at position 16 or Xaa at position 18, but not both, is
      L-Lys or L-Arg
<220> FEATURE:
<221> NAME/KEY: VARIANT
<222> LOCATION: (19)..(19)
<223> OTHER INFORMATION: Xaa at position 19 is any L- or D- amino acid
      other than L-Lys, D-Lys, L-Arg or D-Arg

<400> SEQUENCE: 3

Xaa Xaa Xaa Xaa Xaa Xaa Xaa Xaa Xaa Xaa Xaa Arg Xaa Lys Xaa Xaa
1               5                   10                  15

Xaa Xaa Xaa Arg
            20

<210> SEQ ID NO 4
<211> LENGTH: 20
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (1)..(1)
<223> OTHER INFORMATION: Xaa at position 1 is absent or present and may
      be any  D-amino acid other than D-Lys or D-Arg
<220> FEATURE:
<221> NAME/KEY: VARIANT
<222> LOCATION: (2)..(2)
<223> OTHER INFORMATION: Xaa at position 2 is absent or present and may
      be any L- or D-amino acid other than L-Lys, D-Lys, L-Arg or D-Arg
<220> FEATURE:
<221> NAME/KEY: VARIANT
<222> LOCATION: (3)..(3)
<223> OTHER INFORMATION: Xaa at position 3 is absent or present and may
      be any L- or D-amino acid other than L-Lys, D-Lys, L-Arg or D-Arg
<220> FEATURE:
<221> NAME/KEY: VARIANT
<222> LOCATION: (4)..(4)
<223> OTHER INFORMATION: Xaa at position 4 is absent or present and may
      be any L- or D-amino acid other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is absent or present and may
      be any L- or D-amino acid other than L-Lys, D-Lys, L-Arg or D-Arg
<220> FEATURE:
<221> NAME/KEY: VARIANT
<222> LOCATION: (6)..(6)
<223> OTHER INFORMATION: Xaa at position 6 is absent or present and may
      be any L- or D-amino acid other than L-Lys, D-Lys, L-Arg or D-Arg
<220> FEATURE:
<221> NAME/KEY: VARIANT
```

```
<222> LOCATION: (7)..(7)
<223> OTHER INFORMATION: Xaa at position 7 is absent or present and may
      be any L- or D-amino acid other than L-Lys, D-Lys, L-Arg or D-Arg
<220> FEATURE:
<221> NAME/KEY: VARIANT
<222> LOCATION: (8)..(8)
<223> OTHER INFORMATION: Xaa at position 8 is absent or present and may
      be any L- or D-amino acid other than L-Lys, D-Lys, L-Arg or D-Arg
<220> FEATURE:
<221> NAME/KEY: VARIANT
<222> LOCATION: (9)..(9)
<223> OTHER INFORMATION: Xaa at position 9 is absent or present and may
      be any L- or D-amino acid other than L-Lys, D-Lys, L-Arg or D-Arg
<220> FEATURE:
<221> NAME/KEY: VARIANT
<222> LOCATION: (10)..(10)
<223> OTHER INFORMATION: Xaa at position 10 is absent or present and may
      be any L- or D-amino acid other than L-Lys, D-Lys, L-Arg or D-Arg
<220> FEATURE:
<221> NAME/KEY: VARIANT
<222> LOCATION: (11)..(11)
<223> OTHER INFORMATION: Xaa at position 11 is absent or present and may
      be any L- or D-amino acid other than L-Lys, D-Lys, L-Arg or D-Arg
<220> FEATURE:
<221> NAME/KEY: VARIANT
<222> LOCATION: (12)..(12)
<223> OTHER INFORMATION: Xaa at position 12 is D-Arg
<220> FEATURE:
<221> NAME/KEY: VARIANT
<222> LOCATION: (13)..(13)
<223> OTHER INFORMATION: Xaa at position 13 is any L- or D- amino acid
      other than L-Lys, D-Lys, L-Arg or D-Arg
<220> FEATURE:
<221> NAME/KEY: VARIANT
<222> LOCATION: (14)..(14)
<223> OTHER INFORMATION: Xaa at position 14 is D-Lys
<220> FEATURE:
<221> NAME/KEY: VARIANT
<222> LOCATION: (15)..(15)
<223> OTHER INFORMATION: Xaa at position 15 is any L- or D- amino acid
      other than L-Lys, D-Lys, L-Arg or D-Arg
<220> FEATURE:
<221> NAME/KEY: VARIANT
<222> LOCATION: (16)..(16)
<223> OTHER INFORMATION: Xaa at position 16 is any L- or D- amino acid
      other than L-Lys, D-Lys, L-Arg or D-Arg, subject to the proviso
      that Xaa at position 16 or Xaa at position 18, but not both, is
      D-Lys or D-Arg
<220> FEATURE:
<221> NAME/KEY: VARIANT
<222> LOCATION: (17)..(17)
<223> OTHER INFORMATION: Xaa at position 17 is any L- or D- amino acid
      other than L-Lys, D-Lys, L-Arg or D-Arg
<220> FEATURE:
<221> NAME/KEY: VARIANT
<222> LOCATION: (18)..(18)
<223> OTHER INFORMATION: Xaa at position 18 is any L- or D- amino acid
      other than L-Lys, D-Lys, L-Arg or D-Arg, subject to the proviso
      that Xaa at position 16 or Xaa at position 18, but not both, is
      D-Lys or D-Arg
<220> FEATURE:
<221> NAME/KEY: VARIANT
<222> LOCATION: (19)..(19)
<223> OTHER INFORMATION: Xaa at position 19 is any L- or D- amino acid
      other than L-Lys, D-Lys, L-Arg or D-Arg
<220> FEATURE:
<221> NAME/KEY: VARIANT
<222> LOCATION: (20)..(20)
<223> OTHER INFORMATION: Xaa at position 20 is D-Arg

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```

-continued

```
<210> SEQ ID NO 5
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (2)..(2)
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: (4)..(4)
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is any L- or D- amino acid
      other than L-Lys, D-Lys, L-Arg or D-Arg, subject to the proviso
      that Xaa at position 5 or Xaa at position 7, but not both, is
      L-Lys or L-Arg
<220> FEATURE:
<221> NAME/KEY: VARIANT
<222> LOCATION: (6)..(6)
<223> OTHER INFORMATION: Xaa at position 6 is any L- or D- amino acid
      other than L-Lys, D-Lys, L-Arg or D-Arg
<220> FEATURE:
<221> NAME/KEY: VARIANT
<222> LOCATION: (7)..(7)
<223> OTHER INFORMATION: Xaa at position 7 is any L- or D- amino acid
      other than L-Lys, D-Lys, L-Arg or D-Arg, subject to the proviso
      that Xaa at position 5 or Xaa at position 7, but not both, is
      L-Lys or L-Arg
<220> FEATURE:
<221> NAME/KEY: VARIANT
<222> LOCATION: (8)..(8)
<223> OTHER INFORMATION: Xaa at position 8 is any L- or D- amino acid
      other than L-Lys, D-Lys, L-Arg or D-Arg

<400> SEQUENCE: 5

Arg Xaa Lys Xaa Xaa Xaa Xaa Xaa Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (1)..(1)
<223> OTHER INFORMATION: Xaa at position 1 is D-Arg
<220> FEATURE:
<221> NAME/KEY: VARIANT
<222> LOCATION: (2)..(2)
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: (3)..(3)
<223> OTHER INFORMATION: Xaa at position 1 is D-Lys
<220> FEATURE:
<221> NAME/KEY: VARIANT
<222> LOCATION: (4)..(4)
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: (5)..(5)
<223> OTHER INFORMATION: Xaa at position 5 is any L- or D- amino acid
      other than L-Lys, D-Lys, L-Arg or D-Arg, subject to the proviso
      that Xaa at position 5 or Xaa at position 7, but not both, is
      D-Lys or D-Arg
<220> FEATURE:
```

```
<221> NAME/KEY: VARIANT
<222> LOCATION: (6)..(6)
<223> OTHER INFORMATION: Xaa at position 6 is any L- or D- amino acid
      other than L-Lys, D-Lys, L-Arg or D-Arg
<220> FEATURE:
<221> NAME/KEY: VARIANT
<222> LOCATION: (7)..(7)
<223> OTHER INFORMATION: Xaa at position 7 is any L- or D- amino acid
      other than L-Lys, D-Lys, L-Arg or D-Arg, subject to the proviso
      that Xaa at position 5 or Xaa at position 7, but not both, is
      D-Lys or D-Arg
<220> FEATURE:
<221> NAME/KEY: VARIANT
<222> LOCATION: (8)..(8)
<223> OTHER INFORMATION: Xaa at position 8 is any L- or D- amino acid
      other than L-Lys, D-Lys, L-Arg or D-Arg
<220> FEATURE:
<221> NAME/KEY: VARIANT
<222> LOCATION: (9)..(9)
<223> OTHER INFORMATION: Xaa at position 9 is D-Arg

<400> SEQUENCE: 6

Xaa Xaa Xaa Xaa Xaa Xaa Xaa Xaa Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 7

Arg Tyr Lys Xaa Phe Ile Lys Tyr Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 8

Arg Tyr Lys Xaa Phe Ile Lys Tyr Arg Xaa
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 9

Arg Tyr Lys Xaa Ala Ile Lys Tyr Arg
```

```
<210> SEQ ID NO 10
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 10

Arg Tyr Lys Xaa Ala Ile Lys Tyr Arg Xaa
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 11

Arg Tyr Lys Xaa Arg Ile Ala Tyr Arg
1               5

<210> SEQ ID NO 12
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 12

Arg Tyr Lys Xaa Arg Ile Ala Tyr Arg Xaa
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 13

Arg Tyr Lys Xaa Arg Ile Phe Tyr Arg
1               5
```

```
<210> SEQ ID NO 14
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 14

Arg Tyr Lys Xaa Arg Ile Phe Tyr Arg Xaa
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 15

Arg Tyr Lys Xaa Lys Phe Ile Tyr Arg
1               5

<210> SEQ ID NO 16
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 16

Arg Tyr Lys Xaa Lys Phe Ile Tyr Arg Xaa
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 17

Arg Tyr Lys Xaa Phe Ile Arg Tyr Arg
1               5

<210> SEQ ID NO 18
<211> LENGTH: 10
<212> TYPE: PRT
```

```
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 18

Arg Tyr Lys Xaa Phe Ile Arg Tyr Arg Xaa
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val

<400> SEQUENCE: 19

Arg Tyr Lys Xaa Arg Phe Ile Tyr Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 20

Arg Tyr Lys Xaa Arg Phe Ile Tyr Arg Xaa
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Ile

<400> SEQUENCE: 21

Arg Met Lys Xaa Val Met Lys Phe Arg
1               5

<210> SEQ ID NO 22
<211> LENGTH: 10
<212> TYPE: PRT
<213> ORGANISM: Artificial Sequence
<220> FEATURE:
<223> OTHER INFORMATION: Artificial C6S binding peptide
```

```
<220> FEATURE:
<221> NAME/KEY: VARIANT
<222> LOCATION: (4)..(4)
<223> OTHER INFORMATION: Xaa at position 4 is D-Ile
<220> FEATURE:
<221> NAME/KEY: VARIANT
<222> LOCATION: (10)..(10)
<223> OTHER INFORMATION: Xaa at position 10 is D-His

<400> SEQUENCE: 22

Arg Met Lys Xaa Val Met Lys Phe Arg Xaa
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Phe

<400> SEQUENCE: 23

Arg Phe Lys Xaa Phe Phe Lys Phe Arg
1               5

<210> SEQ ID NO 24
<211> LENGTH: 10
<212> TYPE: PRT
<213> ORGANISM: Artificial Sequence
<220> FEATURE:
<223> OTHER INFORMATION: Artificial C6S binding peptide
<220> FEATURE:
<221> NAME/KEY: VARIANT
<222> LOCATION: (4)..(4)
<223> OTHER INFORMATION: Xaa at position 4 is D-Phe
<220> FEATURE:
<221> NAME/KEY: VARIANT
<222> LOCATION: (10)..(10)
<223> OTHER INFORMATION: Xaa at position 10 is D-His

<400> SEQUENCE: 24

Arg Phe Lys Xaa Phe Phe Lys Phe Arg Xaa
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Artificial TAT peptide control

<400> SEQUENCE: 25

Arg Lys Lys Arg Arg Gln Arg Arg
1               5

<210> SEQ ID NO 26
<211> LENGTH: 9
<212> TYPE: PRT
<213> ORGANISM: Artificial Sequence
<220> FEATURE:
<223> OTHER INFORMATION: Artificial Arg peptide control

<400> SEQUENCE: 26

Arg Arg Arg Arg Arg Arg Arg Arg Arg
1               5
```

```
<210> SEQ ID NO 27
<211> LENGTH: 10
<212> TYPE: PRT
<213> ORGANISM: Artificial Sequence
<220> FEATURE:
<223> OTHER INFORMATION: Artificial C6S negative peptide
<220> FEATURE:
<221> NAME/KEY: VARIANT
<222> LOCATION: (4)..(4)
<223> OTHER INFORMATION: Xaa at position 4 is D-Val
<220> FEATURE:
<221> NAME/KEY: VARIANT
<222> LOCATION: (10)..(10)
<223> OTHER INFORMATION: Xaa at position 10 is D-His

<400> SEQUENCE: 27

Arg Tyr Lys Xaa Phe Ile Lys Pro Arg Xaa
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Artificial C6S negative peptide
<220> FEATURE:
<221> NAME/KEY: VARIANT
<222> LOCATION: (4)..(4)
<223> OTHER INFORMATION: Xaa at position 4 is D-Val

<400> SEQUENCE: 28

Arg Tyr Phe Xaa Arg Ile Lys Tyr Arg
1               5

<210> SEQ ID NO 29
<211> LENGTH: 5
<212> TYPE: PRT
<213> ORGANISM: Artificial Sequence
<220> FEATURE:
<223> OTHER INFORMATION: Linker Sequence

<400> SEQUENCE: 29

Gly Gly Gly Gly Gly
1               5

<210> SEQ ID NO 30
<211> LENGTH: 4
<212> TYPE: PRT
<213> ORGANISM: Artificial Sequence
<220> FEATURE:
<223> OTHER INFORMATION: Linker Sequence

<400> SEQUENCE: 30

Gly Gly Gly Gly
1

<210> SEQ ID NO 31
<211> LENGTH: 9
<212> TYPE: PRT
<213> ORGANISM: Artificial Sequence
<220> FEATURE:
<223> OTHER INFORMATION: Artificial C6S negative peptide

<400> SEQUENCE: 31

Arg Gly Lys Pro Arg Phe Tyr Gln Arg
1               5

<210> SEQ ID NO 32
<211> LENGTH: 9
```

```
<212> TYPE: PRT
<213> ORGANISM: Artificial Sequence
<220> FEATURE:
<223> OTHER INFORMATION: Artificial C6S negative sequence
<220> FEATURE:
<221> NAME/KEY: VARIANT
<222> LOCATION: (4)..(4)
<223> OTHER INFORMATION: Xaa at position 4 is D-Pro

<400> SEQUENCE: 32

Arg Gly Lys Xaa Arg Phe Tyr Gln Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Artificial C6S binding peptide

<400> SEQUENCE: 33

Arg Phe Lys Gly Ser Trp Lys Tyr Arg
1               5
```